United States Patent
Wang et al.

(10) Patent No.: US 9,969,799 B2
(45) Date of Patent: May 15, 2018

(54) ANTI-HUMAN PROBDNF MONOCLONAL ANTIBODY, AND USES THEREOF IN PAINS

(71) Applicant: SHANGHAI YILE BIOTECHNOLOGY LIMITED, Shanghai (CN)

(72) Inventors: Huamao Wang, Shanghai (CN); Ruping Dai, Shanghai (CN); Zonghai Li, Shanghai (CN)

(73) Assignee: Shanghai Yile Biotechnology Limited, Shanghai (CN)

( * ) Notice: Subject to any disclaimer, the term of this patent is extended or adjusted under 35 U.S.C. 154(b) by 0 days. days.

(21) Appl. No.: 15/112,109

(22) PCT Filed: Jan. 4, 2015

(86) PCT No.: PCT/CN2015/070011
§ 371 (c)(1),
(2) Date: Jul. 15, 2016

(87) PCT Pub. No.: WO2015/106641
PCT Pub. Date: Jul. 23, 2015

(65) Prior Publication Data
US 2016/0376359 A1  Dec. 29, 2016

(30) Foreign Application Priority Data

Jan. 15, 2014 (CN) .......................... 2014 1 0015890

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 2003/0087804 A1* | 5/2003 | Hempstead | A61K 38/08 530/399 |
| 2010/0210523 A1* | 8/2010 | Andersen | C07K 14/4703 514/8.4 |
| 2012/0082671 A1* | 4/2012 | Nykjaer | A61K 38/177 424/139.1 |

FOREIGN PATENT DOCUMENTS

| WO | 2004/056385 A2 | 7/2004 |
| WO | 2008/002572 A2 | 1/2008 |
| WO | 2008/074329 A2 | 6/2008 |

OTHER PUBLICATIONS

International Search Report corresponding to PCT/CN2015/070011 dated Apr. 1, 2015; 2 pages.
Li, Pingping et al., "Progress in pro-BDNF," Chinese J Forensic Med, vol. 26, No. 3, 2011, pp. 207-209.
Yang, Longqiu et al., "Regulation of brain-derived neurotrophic factor and its precursor on the pain," Chinese Doctoral Dissertations Full-text Database, No. 11, Nov. 15, 2010, pp. 1-103.
Dieni, S. et al.; "BDNF and its pro-peptide are stored in presynaptic dense core vesicles in brain neurons"; J. Cell Biol.; vol. 196, No. 6; 2012; pp. 775-788.
Marler, K. et al.; "Pro-neurotrophins secreted from retinal ganglion cell axons are necessary for ephrinA-p75$^{NTR}$—mediated axon guidance"; Neural Development; vol. 5, No. 30; 2010; 9 pages.
Wang, H. et al.; "Axonal transport of BDNF precursor in primary sensory neurons"; European Journal of Neuroscience; vol. 24; 2006; pp. 2444-2452.
Yang, J. et al.; "Neuronal release of proBDNF" and Supplements; Nat. Neurosci.; vol. 12, No. 2; Feb. 2009; pp. 113-115.

* cited by examiner

*Primary Examiner* — John D Ulm
(74) *Attorney, Agent, or Firm* — Kilpatrick Townsend & Stockton LLP

(57) ABSTRACT

The present invention provides an anti-human proBDNF monoclonal antibody, and uses thereof in pains. Specifically, the present invention provides uses of antibody polypeptide of tenth to 128$^{th}$ amino acid in a specific recognition pro-BDNF precursor protein structural domain, a nucleic acid sequence for coding the antibody polypeptide, a carrier comprising the nucleic acid sequence, a host comprising the carrier, a pharmaceutical composition comprising the antibody, and the antibody in the preparation of drugs used for alleviating and/or suppressing chronic pains.

16 Claims, 7 Drawing Sheets

SEQUENCE LISTING

```
<160> NUMBER OF SEQ ID NOS: 32

<210> SEQ ID NO 1
<211> LENGTH: 8
<212> TYPE: PRT
<213> ORGANISM: Homo sapiens

<400> SEQUENCE: 1

Gly Phe Thr Phe Thr Asp Tyr Tyr
1               5

<210> SEQ ID NO 2
<211> LENGTH: 10
<212> TYPE: PRT
<213> ORGANISM: Homo sapiens

<400> SEQUENCE: 2

Ile Arg Asn Lys Ala Asn Gly Tyr Thr Thr
1               5                   10

<210> SEQ ID NO 3
<211> LENGTH: 6
<212> TYPE: PRT
<213> ORGANISM: Homo sapiens

<400> SEQUENCE: 3

Ala Ile Thr Met Asp Tyr
1               5

<210> SEQ ID NO 4
<211> LENGTH: 6
<212> TYPE: PRT
<213> ORGANISM: Homo sapiens

<400> SEQUENCE: 4

Gly Asn Ile His Asn Tyr
1               5

<210> SEQ ID NO 5
<211> LENGTH: 7
<212> TYPE: PRT
<213> ORGANISM: Homo sapiens

<400> SEQUENCE: 5
```

```
Asn Ala Gln Thr Leu Ala Asp
1               5

<210> SEQ ID NO 6
<211> LENGTH: 9
<212> TYPE: PRT
<213> ORGANISM: Homo sapiens

<400> SEQUENCE: 6

Gln His Phe Trp Ser Thr Pro Phe Thr
1               5

<210> SEQ ID NO 7
<211> LENGTH: 115
<212> TYPE: PRT
<213> ORGANISM: Homo sapiens

<400> SEQUENCE: 7

Glu Val Lys Val Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Gly Lys Ala Leu Glu Trp Leu
        35                  40                  45

Gly Phe Ile Arg Asn Lys Ala Asn Gly Tyr Thr Thr Glu Tyr Ser Ser
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Ile Thr Met Asp Tyr Trp Gly Gln Gly Thr Ser Val Thr
            100                 105                 110

Val Ser Ser
        115

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Lys Lys Gln Gly Lys Ser Pro His Leu Leu Val
        35                  40                  45

Tyr Asn Ala Gln Thr Leu Ala Asp Gly Val Pro Ser Arg Phe Ser Gly
    50                  55                  60

Ser Ala Ser Gly Thr Gln Tyr Ser Leu Lys Ile Asp Ser Leu Gln Pro
65                  70                  75                  80

Glu Asp Phe Gly Ser Tyr Tyr Cys Gln His Phe Trp Ser Thr Pro Phe
                85                  90                  95

Thr Phe Gly Ser Gly Thr Lys Leu Glu Ile Lys Arg
            100                 105

<210> SEQ ID NO 9
<211> LENGTH: 463
```

<212> TYPE: PRT
<213> ORGANISM: Homo sapiens

<400> SEQUENCE: 9

```
Met Arg Val Leu Ile Leu Leu Trp Leu Phe Thr Ala Phe Pro Gly Phe
1               5                   10                  15

Leu Ser Glu Val Lys Val Val Glu Ser Gly Gly Gly Leu Val Gln Pro
            20                  25                  30

Gly Gly Ser Leu Arg Leu Ser Cys Ala Thr Ser Gly Phe Thr Phe Thr
        35                  40                  45

Asp Tyr Tyr Met Ser Trp Val Arg Gln Pro Pro Gly Lys Ala Leu Glu
    50                  55                  60

Trp Leu Gly Phe Ile Arg Asn Lys Ala Asn Gly Tyr Thr Thr Glu Tyr
65                  70                  75                  80

Ser Ser Ser Val Lys Gly Arg Phe Thr Ile Ser Arg Asp Asn Ser Gln
                85                  90                  95

Ser Ile Leu Tyr Leu Gln Met Asn Thr Leu Arg Ala Glu Asp Ser Ala
            100                 105                 110

Thr Tyr Tyr Cys Ala Ile Thr Met Asp Tyr Trp Gly Gln Gly Thr Ser
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400
```

Gly Gln Pro Glu Asn Asn Tyr Lys Thr Thr Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 10
<211> LENGTH: 236
<212> TYPE: PRT
<213> ORGANISM: Homo sapiens

<400> SEQUENCE: 10

Met Asp Met Met Val Leu Ala Gln Phe Leu Ala Phe Leu Leu Leu Trp
1               5                   10                  15

Phe Pro Gly Ala Arg Cys Asp Ile Gln Met Thr Gln Ser Pro Ala Ser
            20                  25                  30

Leu Ser Ala Ser Val Gly Glu Thr Val Thr Ile Thr Cys Arg Ala Ser
        35                  40                  45

Gly Asn Ile His Asn Tyr Leu Ala Trp Tyr Gln Lys Lys Gln Gly Lys
    50                  55                  60

Ser Pro His Leu Leu Val Tyr Asn Ala Gln Thr Leu Ala Asp Gly Val
65                  70                  75                  80

Pro Ser Arg Phe Ser Gly Ser Ala Ser Gly Thr Gln Tyr Ser Leu Lys
                85                  90                  95

Ile Asp Ser Leu Gln Pro Glu Asp Phe Gly Ser Tyr Tyr Cys Gln His
            100                 105                 110

Phe Trp Ser Thr Pro Phe Thr Phe Gly Ser Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 345
<212> TYPE: DNA
<213> ORGANISM: Homo sapiens

<400> SEQUENCE: 11
gaggtgaagg tggtggagtc tggaggaggc ttggtacagc ctgggggctc tctgagactc      60
tcctgtgcaa cttctgggtt caccttcact gattactaca tgagttgggt ccgccagcct     120
ccaggaaagg cacttgagtg gttgggtttt attagaaaca aagctaatgg ttacacaaca     180

| gagtacagtt catctgtgaa gggtcgattc accatctcca gagataattc ccaaagcatc | 240 |
| ctctatcttc aaatgaacac cctgagagct gaggacagtg ccacttatta ctgtgcaatc | 300 |
| actatggact actggggtca aggaacctca gtcaccgtct cctca | 345 |

<210> SEQ ID NO 12
<211> LENGTH: 324
<212> TYPE: DNA
<213> ORGANISM: Homo sapiens

<400> SEQUENCE: 12

| gacatccaga tgactcagtc tccagcctcc ctatctgcat ctgtgggaga aactgtcacc | 60 |
| atcacatgtc gagcaagtgg gaatattcac aattatttag catggtatca gaagaaacag | 120 |
| ggaaaatctc ctcacctcct ggtctataat gcacaaacct tagcagatgg tgtgccatca | 180 |
| aggttcagtg gcagtgcatc aggaacacaa tattctctca agatcgacag cctgcagcct | 240 |
| gaagattttg ggagttacta ctgtcaacat ttttggagta ctccattcac gttcggctcg | 300 |
| gggacaaagt tggaaataaa acgt | 324 |

<210> SEQ ID NO 13
<211> LENGTH: 1389
<212> TYPE: DNA
<213> ORGANISM: Homo sapiens

<400> SEQUENCE: 13

| atgagagtgc tgattctttt gtggctgttc acagcctttc ctggtttcct gtctgaggtg | 60 |
| aaggtggtgg agtctggagg aggcttggta cagcctgggg gctctctgag actctcctgt | 120 |
| gcaacttctg ggttcacctt cactgattac tacatgagtt gggtccgcca gcctccagga | 180 |
| aaggcacttg agtggttggg ttttattaga aacaaagcta atggttacac aacagagtac | 240 |
| agttcatctg tgaagggtcg attcaccatc tccagagata ttcccaaag catcctctat | 300 |
| cttcaaatga cacctgag agctgaggac agtgccactt attactgtgc aatcactatg | 360 |
| gactactggg gtcaaggaac ctcagtcacc gtctcctcag cctccaccaa gggcccatcg | 420 |
| gtcttccccc tggcaccctc ctccaagagc acctctgggg gcacagcggc cctgggctgc | 480 |
| ctggtcaagg actacttccc cgaaccggtg acggtgtcgt ggaactcagg cgccctgacc | 540 |
| agcggcgtgc acaccttccc ggctgtccta cagtcctcag gactctactc cctcagcagc | 600 |
| gtggtgaccg tgccctccag cagcttgggc acccagacct acatctgcaa cgtgaatcac | 660 |
| aagcccagca acaccaaggt ggacaagaaa gttgagccca atcttgtga caaaactcac | 720 |
| acatgcccac cgtgcccagc acctgaactc ctggggggac cgtcagtctt cctcttcccc | 780 |
| ccaaaaccca aggacaccct catgatctcc cggacccctg aggtcacatg cgtggtggtg | 840 |
| gacgtgagcc acgaagaccc tgaggtcaag ttcaactggt acgtggacgg cgtggaggtg | 900 |
| cataatgcca agacaaagcc gcgggaggag cagtacaaca gcacgtaccg tgtggtcagc | 960 |
| gtcctcaccg tcctgcacca ggactggctg aatggcaagg agtacaagtg caaggtctcc | 1020 |
| aacaaagccc tcccagcccc catcgagaaa accatctcca agccaaagg gcagccccga | 1080 |
| gaaccacagg tgtacaccct gcccccatcc cgggatgagc tgaccaagaa ccaggtcagc | 1140 |
| ctgacctgcc tggtcaaagg cttctatccc agcgacatcg ccgtggagtg ggagagcaat | 1200 |
| gggcagccgg agaacaacta caagaccacg cctcccgtgc tggactccga cggctccttc | 1260 |
| ttcctctata gcaagctcac cgtggacaag agcaggtggc agcaggggaa cgtcttctca | 1320 |

```
tgctccgtga tgcatgaggc tctgcacaac cactacacgc agaagagcct ctccctgtct    1380
ccgggtaaa                                                            1389
```

<210> SEQ ID NO 14
<211> LENGTH: 708
<212> TYPE: DNA
<213> ORGANISM: Homo sapiens

<400> SEQUENCE: 14

```
atggacatga tggtccttgc tcagtttctt gcattcttgt tgctttggtt tccaggtgca      60
agatgtgaca tccagatgac tcagtctcca gcctccctat ctgcatctgt gggagaaact     120
gtcaccatca catgtcgagc aagtgggaat attcacaatt atttagcatg gtatcagaag     180
aaacagggaa aatctcctca cctcctggtc tataatgcac aaaccttagc agatggtgtg     240
ccatcaaggt tcagtggcag tgcatcagga acacaatatt ctctcaagat cgacagcctg     300
cagcctgaag attttgggag ttactactgt caacattttt ggagtactcc attcacgttc     360
ggctcgggga caaagttgga aataaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540 tcccaggaga gtgtcacaga gcaggacagc aaggacagca cctacagcct cagcagcacc     600
ctgacgctga gcaaagcaga ctacgagaaa cacaaagtct acgcctgcga agtcaccccat    660 cagggcctga gctcgcccgt cacaaagagc ttcaacaggg gagagtgt                  708
```

<210> SEQ ID NO 15
<211> LENGTH: 30
<212> TYPE: DNA
<213> ORGANISM: Artificial Sequence
<220> FEATURE:
<223> OTHER INFORMATION: synthetic primer

<400> SEQUENCE: 15

```
gcgaattccc catgaaagaa gcaaacatcc                                       30
```

<210> SEQ ID NO 16
<211> LENGTH: 35
<212> TYPE: DNA
<213> ORGANISM: Artificial Sequence
<220> FEATURE:
<223> OTHER INFORMATION: synthetic primer

<400> SEQUENCE: 16

```
ccgctcgagt tatcttcccc ttttaatggt caatg                                 35
```

<210> SEQ ID NO 17
<211> LENGTH: 36
<212> TYPE: DNA
<213> ORGANISM: Artificial Sequence
<220> FEATURE:
<223> OTHER INFORMATION: synthetic primer

<400> SEQUENCE: 17

```
gctggctagc acccatgaaa gaagcaaaca tccgag                                36
```

<210> SEQ ID NO 18
<211> LENGTH: 28
<212> TYPE: DNA
<213> ORGANISM: Artificial Sequence
<220> FEATURE:
<223> OTHER INFORMATION: synthetic primer

<400> SEQUENCE: 18
ccgctcgagg tggcgccgga ccctcatg                                              28

<210> SEQ ID NO 19
<211> LENGTH: 23
<212> TYPE: DNA
<213> ORGANISM: Artificial Sequence
<220> FEATURE:
<223> OTHER INFORMATION: synthetic primer

<400> SEQUENCE: 19
catggctaca tgctgacagc cta                                                   23

<210> SEQ ID NO 20
<211> LENGTH: 24
<212> TYPE: DNA
<213> ORGANISM: Artificial Sequence
<220> FEATURE:
<223> OTHER INFORMATION: synthetic primer

<400> SEQUENCE: 20
ccagagttcc aggtcactgt cact                                                  24

<210> SEQ ID NO 21
<211> LENGTH: 22
<212> TYPE: DNA
<213> ORGANISM: Artificial Sequence
<220> FEATURE:
<223> OTHER INFORMATION: synthetic primer

<400> SEQUENCE: 21
aggtgctgtc tttgctgtcc tg                                                    22

<210> SEQ ID NO 22
<211> LENGTH: 34
<212> TYPE: DNA
<213> ORGANISM: Artificial Sequence
<220> FEATURE:
<223> OTHER INFORMATION: synthetic primer

<400> SEQUENCE: 22
cgcggatcca cagcctactg atgatcagtc gatg                                       34

<210> SEQ ID NO 23
<211> LENGTH: 24
<212> TYPE: DNA
<213> ORGANISM: Artificial Sequence
<220> FEATURE:
<223> OTHER INFORMATION: synthetic primer

<400> SEQUENCE: 23
ccagggtcac catggagtta gttt                                                  24

<210> SEQ ID NO 24
<211> LENGTH: 23
<212> TYPE: DNA
<213> ORGANISM: Artificial Sequence
<220> FEATURE:
<223> OTHER INFORMATION: synthetic primer

<400> SEQUENCE: 24
gttcaagaag cacacgactg agg                                                   23

<210> SEQ ID NO 25

<210> SEQ ID NO 25
<211> LENGTH: 50
<212> TYPE: DNA
<213> ORGANISM: Artificial Sequence
<220> FEATURE:
<223> OTHER INFORMATION: synthetic primer

<400> SEQUENCE: 25
ggctgttcac agcctttcct ggtttcctgt ctgaggtgaa ggtggtggag                50

<210> SEQ ID NO 26
<211> LENGTH: 38
<212> TYPE: DNA
<213> ORGANISM: Artificial Sequence
<220> FEATURE:
<223> OTHER INFORMATION: synthetic primer

<400> SEQUENCE: 26
cgatgggccc ttggtggagg ctgaggagac ggtgactg                              38

<210> SEQ ID NO 27
<211> LENGTH: 34
<212> TYPE: DNA
<213> ORGANISM: Artificial Sequence
<220> FEATURE:
<223> OTHER INFORMATION: synthetic primer

<400> SEQUENCE: 27
gcctccacca agggcccatc ggtcttcccc ctgg                                  34

<210> SEQ ID NO 28
<211> LENGTH: 23
<212> TYPE: DNA
<213> ORGANISM: Artificial Sequence
<220> FEATURE:
<223> OTHER INFORMATION: synthetic primer

<400> SEQUENCE: 28
cgcttttgag agggagtact cac                                              23

<210> SEQ ID NO 29
<211> LENGTH: 56
<212> TYPE: DNA
<213> ORGANISM: Artificial Sequence
<220> FEATURE:
<223> OTHER INFORMATION: synthetic primer

<400> SEQUENCE: 29
cctagctagc caccatgaga gtgctgattc ttttgtggct gttcacagcc tttcct          56

<210> SEQ ID NO 30
<211> LENGTH: 55
<212> TYPE: DNA
<213> ORGANISM: Artificial Sequence
<220> FEATURE:
<223> OTHER INFORMATION: synthetic primer

<400> SEQUENCE: 30
cttgcattct tgttgctttg gtttccaggt gcaagatgtg acatccagat gactc           55

<210> SEQ ID NO 31
<211> LENGTH: 29
<212> TYPE: DNA
<213> ORGANISM: Artificial Sequence
<220> FEATURE:
<223> OTHER INFORMATION: synthetic primer

<400> SEQUENCE: 31

```
agccaccgta cgttttattt ccaactttg                                        29

<210> SEQ ID NO 32
<211> LENGTH: 56
<212> TYPE: DNA
<213> ORGANISM: Artificial Sequence
<220> FEATURE:
<223> OTHER INFORMATION: synthetic primer

<400> SEQUENCE: 32
gatcgatatc caccatggac atgatggtcc ttgctcagtt tcttgcattc ttgttg          56
```

ANTI-HUMAN PROBDNF MONOCLONAL ANTIBODY, AND USES THEREOF IN PAINS

CROSS-REFERENCE TO RELATED APPLICATIONS

This application is a national phase application under 35 U.S.C. 371 claiming priority to PCT/CN2015/070011, filed Jan. 4, 2015, which application claims priority to CN 201410015890.3, filed Jan. 15, 2014, the teachings of which are hereby incorporated by reference in their entireties for all purposes.

TECHNICAL FIELD

The present invention relates to preparation of a monoclonal antibody against human brain-derived neurotrophic factor precursor protein (proBDNF) and uses of such monoclonal antibody to mitigate and/or inhibit various types of acute and chronic pain, such as post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and the likes.

BACKGROUND

Pain is the fifth vital signs besides body temperature, respiration, heart rate, blood pressure, which can serve as a warning when the body is hurt and cause a series of defensive responses of the body. However, excessive pain will cause damage to the body, and become one kind of unbearable torture to the body. Therefore, analgesia is an important task for healthcare practitioners. Chronic pain threatens the survival and quality of human life, and also causes a great burden on families and society. According to American Pain Society, it was reported that the prevalence of chronic pain in United States was estimated as 35.5%, including 105 million people. It costs over $ 100 billion, directly resulting in the consumption of healthcare spending and the loss of working hours.

The most commonly used analgesics include acetaminophen, non-steroidal anti-inflammatory drugs and opioid receptor agonists, such as tramadol and morphine. Non-steroidal anti-inflammatory drugs (NSAIDs) have weak analgesic efficacy, and may lead to gastrointestinal bleeding, renal failure and liver dysfunction as well as other side effects; and overdose of opioids will cause respiratory depression, and long-term use thereof will lead to side effects, such as constipation, abuse, dependence and addiction. In recent years, there are some other analgesics which are also marketed, for example antidepressants (such as Duloxetine, Lilly), anticonvulsants (such as Puri Galindo, Lyrica™, Pfizer) and selective cyclooxygenase-2 (COX-2) inhibitors (such as Parecoxib, Pfizer).

A new mode for developing analgesic drugs is the mechanism-mediated development of new drug targets. For such mode, the mechanism of pain is mainly studied to find an important factor or target for regulating occurrence and development of pain, thereby developing a new medicament to intervene with the factor or target and achieve analgesia. Many clinical applications based on the results of such basic research are currently tested, however, few of them are successful.

One typical example is the development of anti-nerve growth factor (Nerve Growth Factor, NGF) antibodies. NGF is a member from neurotrophic factor family, and plays an important role in the survival and apoptosis of neuron during development. Basic research shows that NGF may promote pain, therefore blocking NGF may be an important method for treating pain. Therefore many anti-NGF antibodies were developed, including Tanezumab (Pfizer), SAR164877/REGN475 (Sanofi/Regeneron) and NJ-42160443/AMG403 (Johnson & Johnson/Amgen). These drugs show analgesic effects in animal models and clinical trials of phase I/II also show safety and analgesic effects, however, in the clinical trial of phase III in rheumatoid arthritis and ankylosing spondylitis patients for evaluating clinical efficacy and safety of analgesia of anti-NGF antibodies in combination with NSAID drugs, painless ischemic necrosis of caput femoris can be found in a small number of patients (Garber K Painkiller Novel Fate of the mAbs Hangs in Balance. Nat Biotechnol 2011, 173-174; Seidel M, Lane N, Control of Arthritis Pain with Anti-Nerve-Growth Factor, Risk and Benefit, Curr Rheumatol Rep, 2012, 583-585).

Therefore, there is a huge market demand in the development of analgesics with new mechanism. Brain-derived neurotrophic factor BDNF is a neurotrophic factor discovered after nerve growth factor was discovered, molecular weight of which is 12.4 kDa. BNDF mainly distributes in central nervous system, and is also synthesized in peripheral nervous system and plays an important role in the regulation of survival, differentiation of neuron and synaptic plasticity and damage repair. Currently, there is an evidence to show that BDNF is not only an important factor in regulating development of nervous system and emotional disorders, but also an important mediator of pain.

Precursor for brain-derived neurotrophic factor (proBDNF) is synthesized in endoplasmic reticulum from BDNF gene through transcription and translation. The peptide chain is of 247 amino acids in length, and the theoretical molecular weight of the amino acid sequence is 27.8 KD. However, the molecular weight may be varied in a range of 32-36 kD due to different degree of glycosylation for the protein. In ProBDNF, the amino acid sequence at 1-18 positions is signal peptide sequence, and two fragments are produced during secretion process, wherein one fragment is a polypeptide fragment containing amino acids at 19-129 positions (that is, precursor domain), which is called precursor domain (proBDNF pro-domain), and another fragment is a fragment of amino acids at 130-247 positions (that is, mature domain), which will form BDNF with bioactivities upon processing.

At present, a lot of evidence shows that proBDNF is not only an intermediate of mature BDNF, but also can be used as a ligand to bind high-affinity receptor, p75 neurotrophin receptor (p75NTR) for exerting biological effects. Currently, the function of proB DNF-p75NTR signaling pathway in pain is unclear, however, there is a point-of-view that spinal sensitization mechanism of pain is similar to forming mechanism of Long-term potentiation (LTP)/long term depression (LTD) of hippocampus, while BDNF-TrkB and proBDNF-p75NTR signaling pathway are important signaling molecules for regulating LTP/LTD.

In 2012, experiments from Zhang, Yanling (Central South University) demonstrated that the expression of proBDNF in dorsal root ganglion was up-regulated after hind legs of a rat were cut; after an adenoviral vector of proBDNF was injected into hind legs of a rat, a great deal of proBDNF was expressed on nerve fibers by the adenovirus vector, and over-expression of proBDNF caused a significant decrease in withdrawal threshold of hind legs to mechanical stimulation and inflammation in plantar tissue; and withdrawal threshold of hind legs after the hind legs of a rat were cut can be increased by intraperitoneal administration of anti-proBDNF polyclonal antibody.

Cutting pain belongs to acute pain. For acute and chronic pain, both of outer peripheral sensitization and central sensitization can occur, and the difference between which is that: for outer peripheral sensitization, transmitters released by nerve fibers or axons in local tissue and intracellular signaling pathways are different, and pain transmitter and signaling pathways associated with dorsal root ganglion are also different, the latter of which lasts longer; in addition, for central sensitization, sustained activation of glial cells in spinal cord may also be the most important difference between the mechanisms of acute and chronic pain.

SUMMARY OF THE INVENTION

In one aspect, the present invention relates to an antibody polypeptide that specifically recognizes amino acids at positions 19-128 of precursor domain of protein (pro-BDNF pro-domain), including a heavy chain variable region comprising the following amino acid sequence: (a) CDR1 region of SEQ ID NO: 1, CDR2 region of SEQ ID NO: 2, (c) CDR3 region of SEQ ID NO: 3; and/or a light chain variable region comprising the following amino acid sequence: (d) CDR1 region of SEQ ID NO: 4, (e) CDR2 region of SEQ ID NO: 5, (f) CDR3 region of SEQ ID NO: 6. In a specific embodiment, the antibody polypeptide is a monoclonal antibody. In a more specific embodiment, in the antibody polypeptide, the amino acid sequence of heavy chain variable region is SEQ ID NO: 7, and the amino acid sequences of light chain variable region is SEQ ID NO: 8. In another specific embodiment, in the antibody polypeptide, the amino acid sequence of heavy chain is SEQ ID NO: 9, and the amino acid sequence of light chain is SEQ ID NO: 10. In another particular embodiment, the antibody polypeptide may be selected from a humanized antibody polypeptide, a chimeric antibody polypeptide, an affinity maturated antibody polypeptide or one or more combinations thereof. In another particular embodiment, the antibody polypeptide is an antibody polypeptide competing with the antibody polypeptides as said above.

In another aspect, the present invention relates to a nucleic acid sequence encoding the antibody polypeptides as said above. In a specific embodiment, the nucleic acid encoding the amino acid sequence of heavy chain variable region of the antibody polypeptide is SEQ ID NO: 11, and the nucleic acid encoding the amino acid sequence of light chain variable region of the antibody polypeptide is SEQ ID NO: 12. In another specific embodiment, the nucleic acid encoding the amino acid sequence of heavy chain of the antibody polypeptide is SEQ ID NO: 13, and the nucleic acid encoding the amino acid sequence of light chain of the antibody polypeptide is SEQ ID NO: 14.

In another aspect, the present invention relates to a vector comprising the nucleic acid sequence.

In another aspect, the present invention relates to a host comprising the vector.

In another aspect, the present invention relates to a use of one or more of antibody polypeptides specifically recognizing precursor domain of pro-BDNF in preparation of a medicament to mitigate and/or inhibit chronic pain selected from the following group: chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof.

In another aspect, the present invention relates to a use of the antibody polypeptide in preparation of a medicament to mitigate and/or inhibit pain selected from the following group: post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof.

In another aspect, the present invention relates to a pharmaceutical composition comprising an effective amount of the antibody polypeptide. In a specific embodiment, the pharmaceutical composition is administered by intravenous or intraperitoneal injection.

The antibody polypeptide and the corresponding pharmaceutical composition of the present invention are capable of specifically recognizing the precursor domain of proBDNF (pro-domain), inhibiting and/or preventing various types of acute pain or chronic pain, for example, post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof. The antibody polypeptide and the corresponding pharmaceutical composition of the present invention can produce technical effects which can not be achieved in the prior art, and possess broad and good prospects for clinical application.

EMBODIMENTS FOR CARRYING OUT THE INVENTION

Figure 1:
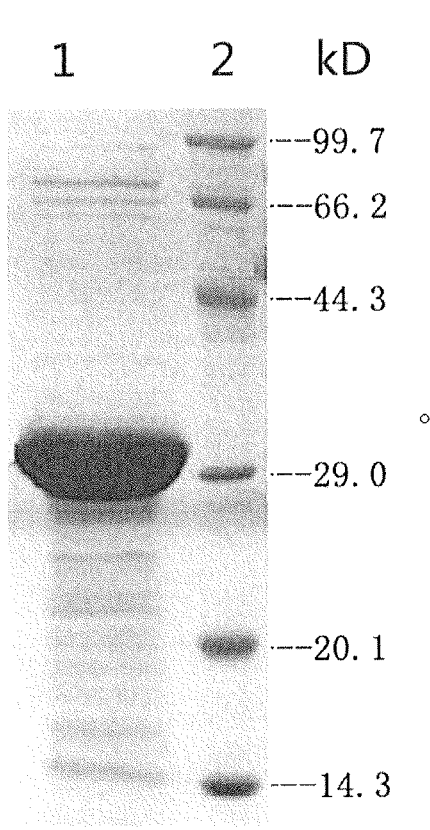
FIG. 1 shows results of SDS-PAGE electrophoresis of purified human proBDNF protein expressed in host strain BL21 (DE3) according to Example 1 of the present invention. 1, purified human proBDNF protein; 2, Protein Molecular Weight Marker (Low), commercially available from TAKARA (Item: 3450).

The anti-proBDNF antibody polypeptide of the present invention can specifically recognizes amino acids at positions 19-128 of precursor domain of pro-BDNF (pro-domain), including a heavy chain variable region comprising the following amino acid sequence: (a) CDR1 region of SEQ ID NO: 1, CDR2 region of SEQ ID NO: 2, (c) CDR3 region of SEQ ID NO: 3; and/or light chain variable region comprising the following amino acid sequence: (d) CDR1 region of SEQ ID NO: 4, (e) CDR2 region of SEQ ID NO: 5, (1) CDR3 region of SEQ ID NO: 6. In each experiment for evaluating pain, mice treated by the antibody, compared with mice in the group of blank control, exhibit significant pain-inhibiting and preventing effects. The antibody polypeptides of the present invention not only inhibit and/or prevent various types of acute pain or chronic pain, for example, post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof.

"Antibody polypeptide" of the present invention refers to an immunoglobulin molecule, which can specifically recognize target sites, such as polysaccharides, polynucleotides, lipids, polypeptides and the likes, through at least one antigen recognition site in the variable region of the immunoglobulin. As used herein, the term "antibody polypeptide" includes intact polyclonal antibodies and monoclonal antibodies, and also includes fragments thereof, e.g., single chain antibody (scFV), Fd fragment, Fab fragment, F(ab')2 fragment, single domain antibody fragment, isolated CDR fragment and derivatives thereof, such as mutants thereof, or immunoglobulin molecule structure comprising modification of at least one antigen binding site.

An intact antibody consists of two identical heavy chains and two identical light chains, each of which contains one variable region (V region) and one or more constant region (C region). The variable region is responsible for binding to an antigen, and the constant region is primarily responsible for binding an effector. In each variable region, there are three flexible rings with highly diversity, called complementary determining region (CDR), which are primarily responsible for antigen-recognition. Other parts of the variable region comprise rigid β sheet and support so-called framework regions (FRs). CDR and FR are spaced to form a sandwich structure.

"Single-chain antibody (scFV) fragment" refers to an antibody fragment constructed by gene engineering, which is a recombinant protein comprising a heavy chain variable region (VH) connecting to a light chain variable region (VL) via a linker, and the two domains are associated via the linker to form an antigen binding site. The size of a scFV is generally ⅙ of a complete antibody.

"Fd fragment" refers to an antibody fragment consisting of heavy chain VH and CH1.

"Fab fragment" refers to a heterodimer consisting of a Fd fragment (consisting of heavy chain VH and CH1) and an entire light chain formed via inter-chain disulfide bonds. The size of "Fab antibody" is ⅓ of an intact antibody, which only contains one antigen binding site.

"F(ab')2 fragment" refers to a bivalent fragment comprising two linked Fab fragments.

"Single domain antibody" consists of a heavy chain variable region or light chain variable region.

The antibody fragment is so named since it only consists of one domain. The size of the fragment is 1/12 of an intact antibody.

"Derivatives" include, for example, derivatives of the antibody obtaining by phage display techniques. Efficiency of phage antibodies binding EGFR or CD3 antigen epitope can be increased by, for example, surface plasmon resonance technology used in BIAcore system (Schier, human antibody hybridomas 7 (1996), 97-105; Malmborg, Immunol. Methods., 183 (1995), 7-13). The method also includes, for example, the preparation method for chimeric antibodies disclosed in WO 89/09622, the preparation method for humanized antibodies disclosed in EP-A10239400 and WO90/07861, and the preparation method for xenogeneic antibodies disclosed in WO91/10741, WO94/02602 and WO96/33735, for example, preparing human antibodies in mice.

The antibody or fragments thereof used in the present invention may be further modified by one of the conventional techniques known in the art or combinations thereof, for example, deletions, insertions, substitutions, additions of amino acids, and/or recombination, and/or other modification methods. The method for introducing such modification into DNA sequence of an antibody according to the amino acid sequence thereof is well known to a skilled person.

The antibody or antibody fragment of the present invention may be humanized, chimeric or murine antibody. As used herein, "humanized antibody" refers to an antibody having an amino acid sequence corresponding to an antibody produced by human, and/or an antibody prepared by techniques for preparing humanized antibody known in the art and disclosed in the present application. Humanized antibody mainly refers to an antibody from a murine (or other non-human) monoclonal antibody, wherein the murine (or other non-human) monoclonal antibody is modified and re-expressed through gene clone, DNA recombination, and most of amino acid sequence of the murine (or other non-human) monoclonal antibody is replaced by a human sequence. And the humanized antibody can substantially maintain the affinity and specificity of the parent murine monoclonal antibody, and also possess reduced heterogenicity, therefore, it is favorable to be applied in human. Humanized antibodies include chimeric antibodies, modified antibody (also named as CDR grafting antibody), surface re-shaped antibodies or fully humanized antibodies.

Humanized antibodies may also be produced by a variety of methods known in the art. For example, a humanized antibody can be selected from a phage library expressing humanized antibodies. Humanized antibodies can also be prepared by introducing human immunoglobulin loci in transgenic animals. The transgenic animal can be, for example, a mouse, genes of endogenous immunoglobulin of which have been partially or completely inactivated. Furthermore, humanized antibodies may also be prepared by immortalizing human B lymphocytes producing antibodies against a specific antigen.

"Chimeric antibody" refers to an antibody, wherein a portion of the amino acid sequence of heavy chain and light chain is homologous to the corresponding sequence of an antibody from a particular species, while other portions of the chain is homologous to the corresponding sequence from another particular species. Typically, in a chimeric antibody, heavy chain and light chain variable regions are similar to variable regions of a mammalian species, while the constant regions are homologous to the sequence from another mammalian species. Advantages of chimeric antibody are that it can be prepared by combining variable regions which can be easily prepared from origins known in the art by using currently available lymphoma cells or B cells of non-human host, and constant regions obtained from, for example a preparation of human cells. The specificity of the chimeric antibody is not affected by its origin, since the constant region thereof is human origin and is not likely to cause immune response in a human recipient. Of course, the definition of chimeric antibody is not limited to the specific examples described herein.

Modified antibody is also named as CDR grafting antibody, wherein CDR in variable region of an antibody is the region of the antibody to recognize and bind antigen and directly determine the specificity of the antibody. CDR of a murine monoclonal antibody is grafted to variable region of a human antibody to replace CDR of the human antibody, therefore, the obtained human antibody will possess antigen-binding specificity of the murine monoclonal antibody and reduced heterogenicity. However, although an antigen mainly contacts with CDR of an antibody, FR region will generally be involved, thereby influencing spatial configuration of CDR. Therefore, after FR region is changed to human FR region, configuration of CDR of the original monoclonal antibody may be altered due to V region formed by such interchimeric murine CDR and human FR, and capability of binding an antigen will be reduced or even significantly reduced. Currently, an antibody can be designed at molecular level, certain key residues in murine FR region can be introduced into human FR region, and if properly configured, affinity of the obtained antibody is comparable with that of the original murine antibody.

surface re-shaped antibody refers to an antibody obtained from humanized modification to surface amino acid residues of a heterologous antibody. Principles of the method are that only regions which are significantly different from those in a human antibody will be replaced, and amino acids which are similar to surface residues of a human antibody are selected for replacement, thereby maintaining activities of an antibody and reducing heterogenicity. Additionally, the replaced segments should not be excessive, and residues which will influence the size of side chain, charge, hydrophobicity, or may form hydrogen bonds thus affecting conformation of complementary determining region (CDR) of an antibody shall not be replaced.

Fully humanized antibody refers to such antibody, which is obtained by transferring an antibody-encoding gene of human into a genetically engineered antibody gene-deleted animal through transgenic or chromosome transfer technology, and the animal expresses human antibodies, thereby obtaining fully humanized antibodies.

As used herein, the term "competition" means that an antibody polypeptide exhibits immunological competitiveness in in vitro experiments, and immunoassay and conditions thereof for immunological competitiveness are well known in the art. An antibody polypeptide competing with the antibody polypeptide of the present invention may include, for example, an antibody polypeptide with similar and/or identical antigen-binding properties obtained by conservatively replacing one or more amino acids in CDR regions (CDR1, CDR2, CDR3) of heavy chain and/or light chain variable region of an antibody polypeptide or one or more amino acids in frame regions of an antibody polypeptide through genetic engineering methods known in the art.

In another aspect, the present invention relates to a vector comprising a nucleotide sequence encoding the above polypeptide. The vector can be an eukaryotic vector or a prokaryotic vector, as long as the vector satisfies the following requirements: (a) coding sequence of the vector contains the sequence for replication initiation, so that the vector can be replicated in a host cell, (b) the vector comprises a gene sequence encoding a selectable marker, and the protein encoded by the gene is essential for the host cell to grow and survive in a selective medium. If the host cell is not transformed or transfected with a vector containing the gene, the host cell can not survive in a particular selective medium. Proteins encoded by a typical selection marker genes include proteins tolerant to an antibiotic or toxin, such as antibiotics or toxins including, for example ampicillin, kanamycin, tetracycline, neomycin, hygromycin, methotrexate and the like; proteins for compensating auxotroph for supplying critical nutrients not present in the culture medium, e.g., gene encoding D-alanine racemase. Examples of resistance-screening include transfection of an exogenous vector containing neomycin resistance gene, so that the host cell can survive in the medium containing neomycin, or G418. Another example is using dihydrofolate reductase (DHFR) selectable marker in a mammalian cell, such as Chinese Hamster Ovary (CHO) cell. The mammalian cell refers to a DHFR deficient cell, in which the gene of dihydrofolate reductase is not contained and nucleic acids can not be synthesized, therefore, it must be grown in a medium containing HT. When a host cell is transfected using a vector, a positive clone containing an exogenous vector comprising both of target gene and DHFR gene can be obtained by selecting under the above culture conditions. (c) the coding sequence of the vector comprises a promoter sequence, (d) the expression vector can further comprise other sequences, including signal peptide sequence, transcription termination sequence, enhancer sequence and the like. Preferably, the vector of the present invention is a eukaryotic vector. Preferably, the vector of the present invention is a pH vector for the eukaryotic expression of an antibody, which contains CMV promoter, internal ribosome entry site sequence (IRES), DHFR selection markers and other components. Methotrexate (MTX) is a DHFR inhibitor which can block the function of DHFR. When the cell culture medium contains MTX, DHFR is inhibited. The gene can be self-amplified by feedback regulation, so that genes at upstream and downstream will be amplified, therefore, target genes will be amplified, thereby increasing the expression of the target protein.

In another aspect, the present invention relates to a vector comprising the host cell for expressing desired multifunctional antibody polypeptides. "Host cell" includes a single cell or a cell culture, which can receive and have received a vector comprising inserted polynucleotide.

According to used vectors, the host cell of the present invention may be any prokaryotic host cell or eukaryotic host cell. Eukaryotic host cells, including yeast, insect cells, plant cells, mammalian cells may be preferred, since complex post-translational modification (e.g. glycosylation) of the target protein is present in a eukaryotic cell, and more and more of eukaryotic cells are used in large-scale cultivation. Common host cell lines include monkey kidney cells (COS-7 ATCC CRL 1651), human embryonic kidney 293 cells and subcloned cell lines, baby hamster kidney cells (BHK, ATCC CCL10), Chinese hamster ovary (CHO) cells and the like. Preferably, the eukaryotic host cell of the present invention is a Chinese hamster ovary cells.

The present invention relates to a use of one or more of antibody polypeptides specifically recognizing precursor domain of pro-BDNF in preparation of a medicament to mitigate and/or inhibit chronic pain selected from the following group: chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof.

The present invention also relates to a use of one or more of antibody polypeptide that specifically recognizes amino acids at positions 19-128 of precursor domain of pro-BDNF in preparation of a medicament to mitigate and/or inhibit acute or chronic pain selected from the following group: post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof.

The present invention further includes a pharmaceutical composition comprising said antibody polypeptides. The composition may also contain a pharmaceutically acceptable carrier. The pharmaceutical composition may be administered by conventional routes, including but not limited to, intravenous, intraperitoneal injection. The pharmaceutical composition of the invention may also be used in combination with other agents for inhibiting/preventing pain.

The "effective amount" of the drug, compound or pharmaceutical composition of the present invention refers to an amount sufficient to produce advantageous and desired results, and the results include clinical outcomes of reducing or mitigating pain. An effective amount can be administered by one or several administrations. For the purposes of the present invention, an effective amount means an amount sufficient to treat, reduce, decrease, and inhibit intensity of pain and/or prevent pain. As appreciated under clinical conditions, an effective amount of the drug may be determined with or without another drug. Thus, "effective amount" may be considered to be under the conditions of administering one or more agents, or if desired results can be obtained or have been obtained when one single agent is administered in combination with one or more other agents, the single agent can be considered as being administered in an effective amount. Specific dosage should be determined according to factors, such as the route of administration, and patient's condition, which are within the skill of a skilled physician.

The invention will be further illustrated with reference to the following specific examples. It is to be understood that these examples are only intended to illustrate the invention, but not to limit the scope of the invention. For the experimental methods in the following examples without particular conditions, they are performed under routine conditions, such as conditions described in Sambrook et al., Molecular Cloning: A Laboratory Manual, New York: Cold Spring Harbor Laboratory Press, 1989, or as instructed by the manufacturer.

Example 1: Prokaryotic-Expression of Human proBDNF Antigen 1.1 Construction and Identification of pET22b-proBDNF Vector PCR amplification was performed by using the following primers and cDNA of human tumor cell U87MG as template (commercially available from RAYGENE):

```
PROBDNF-F:
                                       (SEQ ID NO: 15)
5' GCGAATTCCCCATGAAAGAAGCAAACATCC 3'

PROBDNF-R:
                                       (SEQ ID NO: 16)
5' CCGCTCGAGTTATCTTCCCCTTTTAATGGTCAATG 3'
``` to obtain PRO BDNF gene fragment (703 bp) with restriction sites ECORI/XhoI at both ends. The desired gene fragment proBDNF was obtained by double digestion with ECORI/XhoI (commercially available from NEB). Plasmid vector pET22b (commercially available from Novogen) was subject to double digestion with ECORI/XhoI, and vector fragments were recovered through agarose gel electrophoresis and connected to gene fragment proBDNF as said above under the action of T4 ligase (commercially available from NEB). And then *E. coli* TOP10 (commercially available from LIFE) was transformed, and screened according to ampicillin resistance. Positive clones containing inserted fragments were identified by digestion with ECORI/XhoI, and verified by sequencing, thereby obtaining plasmid pET22b-proBDNF for prokaryotic expression containing correct human proBDNF gene sequence.

1.2 Expression and Purification of Human proBDNF Protein

The host strain BL21 (DE3) (commercially available from Novagen) for expression was transformed by pET22b-proBDNF plasmid, and plated on an ampicillin-resistant dish and invertion-cultured at 37° C. overnight. A single clone was picked for induced expression. After a single clone was picked, it was cultured with shaking to $OD_{600}$ 0.6-0.8. Final concentration of 1 mM of IPTG was added at 30° C. for 4 hrs, and bacteria liquid was collected. The precipitate was collected by centrifugation, ⅒ volumes of buffer A (50 mM $NaH_2PO_4$, 300 mM NaCl, 10 mM imidazole, pH 8.0) was added for resuspension, and PMSF was added (final concentration of 1 mM) and processed by ultrasound on ice (3 seconds of ultrasonic-process, 10 seconds of interval, 99 times for each cycle, 4 cycles), and centrifuged (4° C., 12000 g) for 15 mins, and the supernatant was collected by centrifugation, and purified by affinity chromatography through Ni-NTA Agarose column (commercially available from QIAGEN) to obtain the expressed target protein. The solution was dialyzed against PBS, and then the purity of the purified protein after dialysis was analyzed through 12% SDS-PAGE, the content thereof is detected by A280, and a small quantity of sample was taken for detecting its molecular weight through SDS PAGE electrophoresis. According to results of SDS-PAGE shown in FIG. 1, the molecular weight of target bands in the first column is about 30 kD, which is substantially consistent with theoretical molecular weight of proBDNF, 27.8 kD.

Example 2: Eukaryotic-Expression of Human proBDNF Pro-Domain 2.1 Construction of Expression Vector V5F-Pro-Domain of Human proBDNF Pro-Domain PCR amplification was performed by using the following primers and the plasmid pET22b-proBDNF obtained above as template:

```
BDNFproVF1
                                       (SEQ ID NO: 17)
5'GCTGGCTAGCACCCATGAAAGAAGCAAACATCCGAG3'

BDNFproVR1
                                       (SEQ ID NO: 18)
5'CCGCTCGAGGTGGCGCCGGACCCTCATG 3'
``` to obtain a gene fragment (350 bp) of human proBDNF pro-domain with restriction sites NheI/XhoI at both ends. The PCR fragment was subjected to double digestion with NheI/XhoI (commercially available from NEB), and the obtained gene fragment of pro-domain was ligated to vector 5F (commercially available from RAYGENE), which was also subjected to double digestion with NheI/XhoI (commercially available from NEB), by T4 DNA ligase, and used to transform host strain TOP10 (commercially available from LIFE). Positive clones were selected for PCR identification and verified by sequencing, thereby successfully constructing V5F-pro-domain plasmid.

2.2 Expression and Purification of Human proBDNF Pro-Domain

Figure 2:
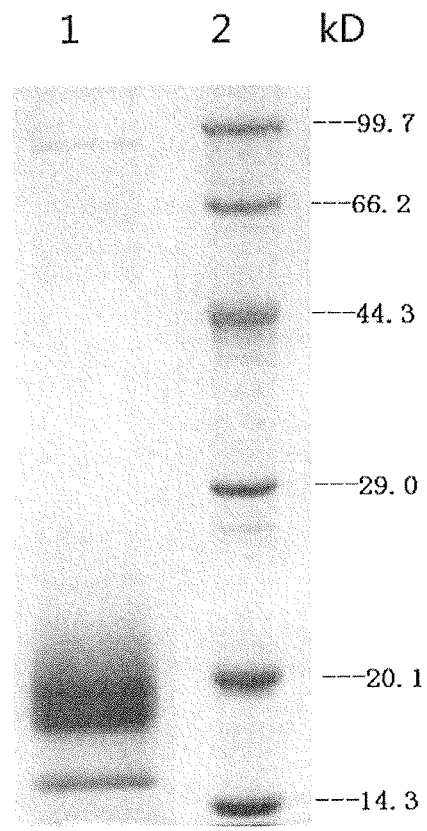
FIG. 2 shows results of SDS-PAGE electrophoresis of purified precursor domain of human proBDNF expressed in HEK293F cell according to Example 2 of the present invention. 1, purified precursor domain of human proBDNF; 2, Protein Molecular Weight Marker (Low), commercially available from TAKARA (Item: 3450).

Well-grown HEK293F cells (HEK293F, commercially available from LIFE) were seeded into a flask of cell culture at $1 \times 10^6$ Cells/ml, and incubated overnight at 37° C., 5% $CO_2$ 120 rpm; V5F-pro-domain plasmid obtained in the above step and liposome (293Fectin, commercially available from LIFE) was diluted with DMEM and gently mixed, and incubated at room temperature for 20 mins. The incubated DNA-liposome complex was added into HEK293F cells, and incubated at 37° C., 5% $CO_2$ 120 rpm for 72 hr. Cell culture fluid was collected and centrifuged at 4500 g for 15 mins, the supernatant was taken and cells were discarded. 1 ml of FLAG antibody affinity filler (ANTI-FLAG Agarose Affinity Gel, purchased from Sigma-Aldrich) was loaded on a column, FLAG affinity column was equilibrated with 5-10 column volumes of lysis buffer (50 mM PB, 0.3M NaCl, 5% glycerol). Upon centrifugation, the supernatant of cell culture flowed through FLAG affinity column at 1 ml/min and the flow-through liquid was stored at 4° C. 5-10 column volumes of washing buffer 1 (50 mM PB, pH 7.8, 0.3 M NaCl, 5% glycerol) was used to wash the column and washing solution 1 was stored at 4° C. 4-5 column volumes of washing buffer 2 (50 mM PB, pH 7.8, 0.5 M NaCl, 5% glycerol) was used to wash the column and washing solution 2 was stored at 4° C. 4-5 column volumes of elution buffer (50 mM Glycine.HCl, pH 3.0, 0.3 M NaCl, 5% glycerol) was used to wash the column, the eluate was collected and neutralization buffer (1 M Tris.HCl pH 8.0) was added, and dialysed against dialysis liquid (50 mM PB, pH 7.8, 0.3 M NaCl, 5% glycerol) overnight at 4° C., and stored. A small amount of sample was taken and subject to SDS PAGE electrophoresis. Electrophoresis results shown in FIG. 2 demonstrate that the molecular weight of the target band in the first column is about 20 kD, slightly larger than the theoretical molecular weight of human proBDNF pro-domain of 13 kD. Without limiting to any theory, it may be relevant to the glycosylation of eukaryotically-expressed protein.

Example 3: Eukaryotic-Expression of Rat proBDNF Pro-Domain-Fc 3.1 Construction of Expression Vector V5F-Rat-Pro-Domain-Fc of Rat proBDNF Pro-Domain-Fc PCR amplification was performed by using the following primers and cDNA of rat as template (commercially available from RAYGENE):

```
RatproF1
                                       (SEQ ID NO: 19)
5'GCTGGCTAGCGCGCCCATGAAAGAAGCAAAC3'

RatproR1
                                       (SEQ ID NO: 20)
5'CCGCTCGAG GCGCCGAACCCTCATAGACATG3'
``` to obtain a gene fragment (356 bp) of rat proBDNF pro-domain with restriction sites NheI/BamHI at both ends. The PCR fragment was subjected to double digestion with NheI/BamHI (commercially available from NEB), and the obtained gene fragment of pro-domain was ligated to vector V5FC for Fc fusion (commercially available from RAYGENE), which was also subjected to double digestion with NheI/BamHI (commercially available from NEB), by T4 DNA ligase, and used to transform host strain TOP10 (commercially available from LIFE). Positive clones were selected for PCR identification and verified by sequencing, thereby successfully constructing V5FC-rat-pro-domain plasmid.

3.2 Expression and Purification of Rat proBDNF Pro-Domain-Fc

Figure 3:
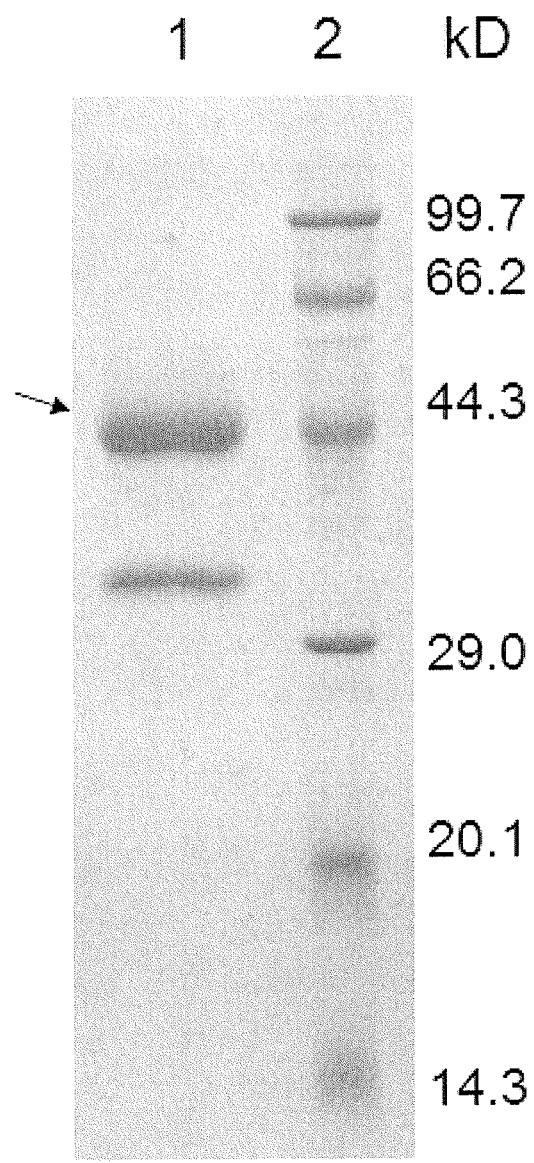
FIG. 3 shows results of SDS-PAGE electrophoresis of purified fused protein of precursor domain of rat proBDNF expressed in HEK293F cell according to Example 3 of the present invention. 1, purified fused protein of precursor domain of rat proBDNF; 2, Protein Molecular Weight Marker (Low), commercially available from TAKARA (Item: 3450).

Well-grown HEK293F cells (HEK293F, commercially available from LIFE) were seeded into a flask of cell culture at $1 \times 10^6$ Cells/ml, and incubated overnight at 37° C., 5% $CO_2$ 120 rpm; V5F-cat-pro-domain plasmid obtained in the above step and liposome (293Fectin, commercially available from LIFE) was diluted with DMEM and gently mixed, and incubated at room temperature for 20 mins. The incubated DNA-liposome complex was added into HEK293F cells, and incubated at 37° C., 5% $CO_2$ 120 rpm for 72 hr. Cell culture fluid was collected and centrifuged at 4500 g for 15 mins, the supernatant was taken and cells were discarded. 1 ml of proteinA affinity filler (proteinA Agarose, purchased from RAYGENE) was loaded on a column, proteinA affinity column was equilibrated with 5-10 column volumes of lysis buffer (50 mM PB, 0.3M NaCl, 5% glycerol). Upon centrifugation, the supernatant of cell culture flowed through proteinA affinity column at 1 ml/min and the flow-through liquid was stored at 4° C. 5-10 column volumes of PBS (20 mM PB, pH 7.8, 0.15 M NaCl) was used to wash the column and washing solution 1 was stored at 4° C. 4-5 column volumes of elution buffer (100 mM Glycine.HCl, pH 2.5) was used to wash the column, the eluate was collected and 10% v/v of neutralization buffer (1 M Tris.HCl pH 8.0) was added, and dialysed against dialysis liquid (50 mM PB, pH 7.8, 0.3 M NaCl, 5% glycerol) overnight at 4° C., and stored. A small amount of sample was taken and subject to SDS PAGE electrophoresis. Electrophoresis results shown in FIG. 3 demonstrate that the molecular weight of the target band in the first column is about 44.3 kD, comparable to the theoretical molecular weight of rat proBDNF pro-domain-Fc.

Example 4: Preparation and Identification of Anti-Human proBDNF Pro-Domain Monoclonal Antibody 4.1 Immunization with Recombinant Protein The 1 ml of purified proBDNF protein (1.0 mg/mL) obtained in Example 1 as an antigen was completely emulsified and mixed with 1 mL of complete Freund's adjuvant (commercially available from by Sigma-Aldrich), and subcutaneously used to immunize 6-8 week-old BALB/c mice, 100 μg of human proBDNF antigen per mouse. After 4 weeks, human proBDNF antigen was emulsified and mixed with incomplete Freund's adjuvant, and used to immunize mice via intraperitoneal injection, per mouse. After an interval of 2 weeks, 50 μg of antigen was used for booster immunization via intraperitoneal injection. 1 week after the $4^{th}$ booster immunization, purified human proBDNF pro-domain obtained in Example 2 was used for coating, mouse anti-serum titer was detected by ELISA. Booster immunization was continued until mouse anti-serum titer>$10^5$. 3 weeks after the last booster immunization, 20 μg of human proBDNF pro-domain as said above was used for immunization in spleen and stored until use.

4.2 Establishment of Human proBDNF Hybridoma Cell Line 4 days after booster immunization in spleen, spleen was taken under sterile conditions. Lymphocytes were isolated through a 100 mesh filter, fused with myeloma cell line SP2/0, and selectively cultured with hypoxanthine, aminopterin and thymidine (HAT) for 3 days. Afterwards, HT medium was supplemented, and cultured for another week. Human proBDNF antigen of the above Examples of the present invention was used for coating, and positive clones were screened through ELISA, and subcloned for 3 times through limiting dilution, and cultured for another 2 months, and finally obtained a stable hybridoma cell line (each clone named as: 2B11, 2C7, 5C10, 4C3, 6F3, 2F3, 8E1, 1G7).

4.3 Purification of Antibody

Clones of hybridoma cells as said above were taken and used to intraperitoneally inject mice in each group at $5×10^5$ cells/mouse for preparing ascites. 100 ml of ascites was taken, and diluted in 2 volumes of 0.06 M sodium acetate buffer pH 4.0. 4% octanoic acid was slowly added dropwise with stirring, and stirred for 30 mins. The obtained turbid liquid was centrifuged at 10000 g for 30 mins. The precipitate was discarded, and the supernatant was dialyzed overnight against 0.01 M phosphate buffer, pH 7.4. The dialysate was taken, and an equal volume of saturated ammonium sulfate was slowly added, and placed for 2 hours. The turbid liquid was centrifuged at 10000 g for 10 mins. The supernatant was discarded, and the precipitate was dissolved with 0.01 M PBS, pH 7.4. Upon dissolution, the solution was dialyzed against 0.01 M PBS, pH 7.4, during which the dialysis liquid was changed twice (the time interval for changing dialysis liquid shall not be less than 5 hours). The dialysate was centrifuged at 10000 g for 10 mins, the precipitate was discarded and the supernatant was collected.

Protein G affinity column (purchased from GE) was used. The column was warmed to room temperature, and equilibrated with 5 column volumes of PBS (0.01 M PB, 0.15 M NaCl, pH 7.4). The collected supernatant as said above was loaded, and 5 column volumes of PBS was used for washing. The column was eluted by 0.1 M glycine-hydrochloric acid solution, pH 2.3 and the eluate was neutralized by 1/10 volume of 1 M disodium hydrogen phosphate solution, pH 9.0. The solution was dialyzed against 0.01 M PBS, pH 7.4, during which the dialysis liquid was changed twice (the time interval for changing dialysis liquid shall be more than 5 hours). The dialysate was centrifuged at 10000 g for 10 mins, the supernatant was filtered through a 0.22 um membrane and stored, thereby obtaining purified monoclonal antibody produced by each corresponding clone.

4.4 Identification of Binding Region of a Monoclonal Antibody by ELISA Assay

Experiment group 1: purified human proBDNF protein obtained in Example 1 was diluted in PBS (0.01 M PB, 0.15 M NaCl, pH 7.4). There are 8 wells for each group corresponding to 8 purified monoclonal antibodies which will be subsequently added, respectively.

Experiment group 2: purified human proBDNF pro-domain obtained in Example 2 was diluted in PBS (0.01 M PB, 0.15 M NaCl, pH 7.4). There are 8 wells for each group corresponding to 8 purified monoclonal antibodies which will be subsequently added, respectively.

In Experiment groups 1 and 2, 50 ul (50 ng) of diluted protein was used for coating overnight at 4° C., respectively. Then the supernatant was discarded, each well was washed with PBS for 2 times, and blocked with PBS containing 5% milk powder at 37° C. for 2 hours. And then, at 37° C., into 8 wells of Experiment groups 1 and 2 was added 50 ul (1 ug/ml) of 8 purified monoclonal antibodies obtained in Example 3.3, respectively for 1 hour. Each well was washed with PBST containing 0.5% Tween-20 for 3 times, and 50 ul of HRP labeled goat anti-mouse secondary antibody was added at 37° C. for 1 hour. Each well was washed with PBST containing 0.5% Tween-20 for 5 times, ABTS chromogenic substrate was added and developed for 15 minutes, and then absorbance value was determined at 405 nm. The experiment was repeated for two times, and the average absorbance value of two measurements was calculated. When the absorbance value is greater than the reading in the negative control well by three times, it was identified as positive.

Figure 4:
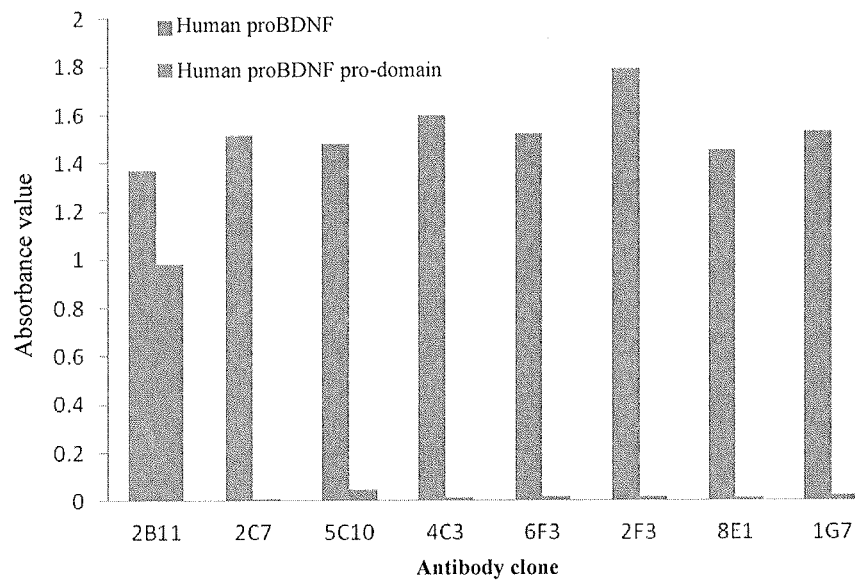
FIG. 4 shows experimental results of specific antigen binding region of anti-proBDNF monoclonal antibody produced by hybridoma cell lines in Example 3 of the present invention against human proBDNF and human proBDNF precursor domain.

As shown in FIG. 4, purified monoclonal antibodies 2B11 binds to human proBDNF and human proBDNF pro-domain, which demonstrates that the antibody 2B11 binds to the common segment of both of the proteins, that is, the region of human proBDNF pro-domain.

4.5 Labeling Monoclonal Antibody 2B11 with Horseradish Peroxidase

At 4° C., 10 mg of horseradish peroxidase (HRP) was dissolved in 1 ml of water, and 1 ml of 0.5 M NaIO4 was added for 30 mins. At 4° C., 1 ml of 0.16 M ethylene glycol was added for 30 mins. 10 mg of 2B11 antibody was dialyzed against 0.05 M carbonate buffer pH 9.5, oxidated HRP and 2B11 antibody were mixed and dialyzed at 4° C. overnight. 0.4 ml of 1 mg/ml NaBH4 was added and stirred at 4° C. for 2 hours. $NaH_2PO_4$ solution of low concentration was used to adjust pH at weak acid, and an equal volume of glycerol was added and stored until use.

4.6 Determination of Species Specificity of Antibody 2B11 Binding proBDNF by ELISA Assay Experiment group 1: purified human proBDNF protein obtained in Example 1 was diluted in PBS (0.01 M PB, 0.15 M NaCl, pH 7.4).

Experiment group 2: prokaryotically-expressed mouse proBDNF (purchased from Alomone labs) was diluted in PBS (0.01 M PB, 0.15 M NaCl, pH 7.4).

Experiment group 3: rat proBDNF pro-domain eukaryotically-expressed in Example 3 was diluted in PBS (0.01 M PB, 0.15 M NaCl, pH 7.4).

50 ul (50 ng) of diluted protein in Experiment group 1, 2 and 3 was used for coating overnight at 4° C., respectively. Then the supernatant was discarded, each well was washed with PBS for 2 times, and blocked with PBS containing 5% milk powder at 37° C. for 2 hours. The supernatant was discarded, and 50 ul of diluted horseradish peroxidase-labeled 2B11 antibody of Example 4.5 (1 ug/ml) was added at 37° C. for 1 hour. The supernatant was discarded, and each well was washed with PBST containing 0.5% Tween-20 for 3 times, ABTS chromogenic substrate was added and developed for 15 minutes, and then absorbance value was determined at 405 nm. When the absorbance value is greater than the reading in the negative control well by three times, it was identified as positive.

Figure 5:
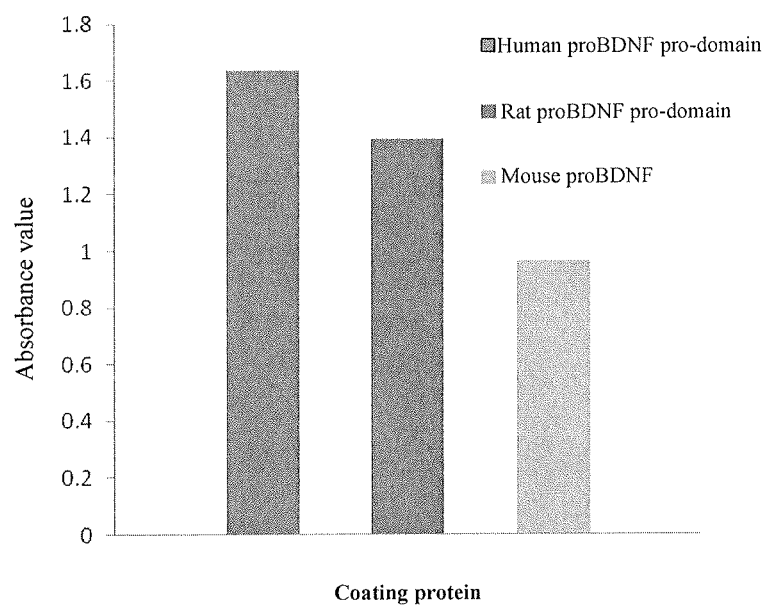
FIG. 5 shows experimental results of specific antigen binding region of anti-proBDNF monoclonal antibody 2B11 in Example 4 of the present invention against human proBDNF precursor domain, rat proBDNF precursor domain and mouse proBDNF.

As shown in FIG. 5, clone 2B11 binds to human proBDNF prepared in Example 1 and commercially purchased murine proBDNF as well as rat proBDNF pro-domain eukaryotically-expressed in Example 3.

Figure 6:
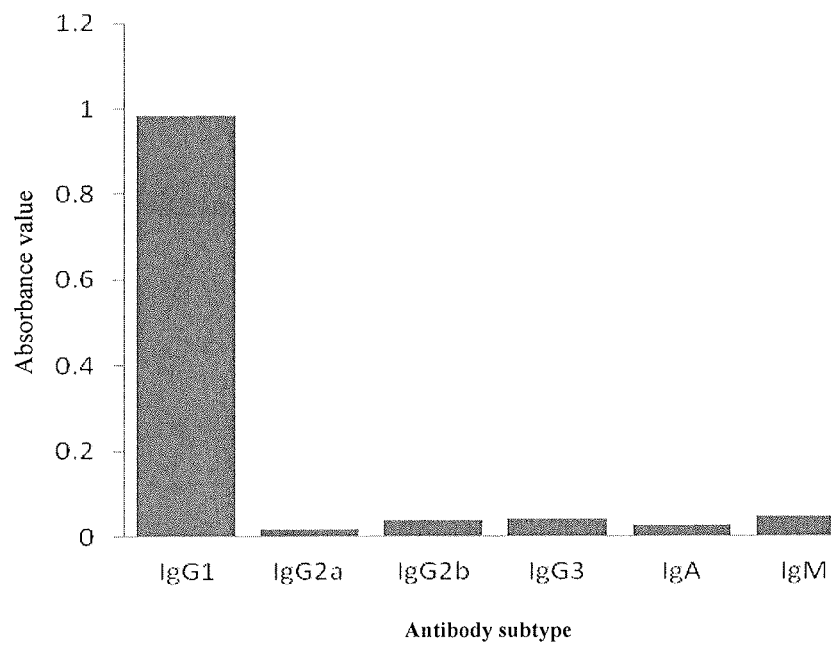
FIG. 6 shows results of subtype analysis on anti-proBDNF monoclonal antibody 2B11 according to Example 3 of the present invention.

4.7 Determination of Antibody Subtype of Clone 2B11 by ELISA Assay 6 experiment groups were established according to the number of isotyping antibodies, wherein, in each group, 50 ul of diluted prokaryotically-expressed human proBDNF protein (50 ng) was added into each well for coating overnight at 4° C. The supernatant was discarded, each well was washed with PBS (0.01 M PB, 0.15 M NaCl, pH 7.4) for 2 times, and blocked with PBS containing 5% milk powder at 37° C. for 2 hours. The supernatant was discarded, and 50 ul of diluted 2B11 antibody purified as above (1 ug/ml) was added into each well at 37° C. for 1 hour. Afterwards, the supernatant was discarded, each well was washed with PBST containing 0.5% Tween-20 for 3 times, and for Experiment groups 1-6, corresponding 6 isotyping antibodies (purchased from Sigma-Aldrich) were added respectively: goat anti-mouse IgG1, goat anti-mouse of IgG2a, goat anti-mouse IgG2b, goat anti-mouse IgG3, goat anti-mouse IgA and goat anti-mouse IgM, at 37° C. for 1 hr. The supernatant was discarded, each well was washed with PBST containing 0.5% Tween-20 for 3 times, and 50 ul of HRP-labeled donkey anti-goat secondary antibody was added at 37° C. for 1 hour. The supernatant was discarded, each well was washed with PBST containing 0.5% Tween-20 for 5 times, ABTS chromogenic substrate was added and developed for 15 minutes, and then absorbance value was determined at 405 nm. When the absorbance value is greater than the reading in the negative control well by three times, it was identified as positive. As shown in FIG. 6, clone 2B11 was identified as IgG1 type.

Example 5. Determination of the Sequence of Monoclonal Antibody 2B11

The sequence of 2B11 was cloned by 5'-RACE method and confirmed by sequencing (details can be found in instructions of Takara 5'-full RACE Kit): 5' phosphate groups exposed in total RNA were dephosphorylated using alkaline phosphatase (CIAP). Total RNA was in an amount of 2 ug, and was recovered by phenol-chloroform extraction after reaction. 5' cap structure of mRNA was removed by using Tobacco Acid Pyrophosphatase (TAP), while remaining a phosphate group. 5' RACE Adaptor is connected to mRNA With T4 RNA ligase, and was recovered by phenol-chloroform extraction after reaction. Reverse transcription reaction was performed with reverse transcriptase, and used primers was Random 9 mers provided in Kit.

The target gene was PCR-amplified by a high fidelity enzyme with the reverse transcription product as a template, and used primers were as follows:

```
5': 5'RACE Outer Primer
                                    (SEQ ID NO: 19)
(CATGGCTACATGCTGACAGCCTA), provided in Kit;

3': Heavy chain: mIgG1-out primer
                                    (SEQ ID NO: 20)
(CCAGAGTTCCAGGTCACTGTCACT)

Light chain: mκ-out primer
                                    (SEQ ID NO: 21)
(AGGTGCTGTCTTTGCTGTCCTG).
```

Nested PCR was performed with above-obtained PCR products as templates, and used primers were as follows:

```
5': 5'RACE Inner Primer
                                    (SEQ ID NO: 22)
(CGCGGATCCACAGCCTACTGATGATCAGTCGATG); provided in
Kit 3': Heavy chain: mIgG1-inner primer
                                    (SEQ ID NO: 23)
(CCAGGGTCACCATGGAGTTAGTTT)

Light chain: mκ-inner primer
                                    (SEQ ID NO: 24)
(GTTCAAGAAGCACACGACTGAGG).
```

PCR products obtained above through amplification was purified and TA-cloning was performed (pGEM-T the Easy Vector Kit, commercially available from Promega, detailed method can be found in the instructions of the kit), thereby obtaining Teasy-2B11 VH and Teasy-2B11V κ vector respectively, which were sequenced to obtain heavy chain and light chain sequences of monoclonal antibodies 2B11. Heavy chain and light chain sequences are shown in SEQ ID NO: 9 and SEQ ID NO: 10 respectively. According Kabat-Man, sequences of heavy chain variable region and light chain variable region can be determined as shown in SEQ ID NO: 7 and SEQ ID NO: 8. According to Kabat numbering rule, sequences of CDR1, CDR2, CDR3 in heavy chain variable region are shown in SEQ ID NO: 1-3 respectively, and sequences of CDR1, CDR2, CDR3 in light chain variable region are determined as shown in SEQ ID NO: 4-6 respectively.

Example 6. Construction of Chimeric Antibody Vectors pH-CH2B11 and pK-CH2B11 and Preliminary Identification of Binding Activities 6.1 Construction of Vector pH-CH2B11

PCR amplification was performed using following primers with vector Teasy-2B11VH constructed in Example 5 of the present invention as a template,

```
2BVHF
                                    SEQ ID NO: 25
(5'-ggctgttcacagcctttcctggtttcctgtct gaggtgaaggtg
gtggag-3'),
and 2BVHR
                                    SEQ ID NO: 26
(5'-cgatgggcccttggtggaggctgaggagacggtgactg-3'),
``` thereby obtaining heavy chain variable region of 2B11 antibody.

PCR amplification was performed with antibody vector pH-EGFRvIII (that is, pH-CH12, construction of which can be found in Example 7.1 of PCT/CN2009/074090),

```
Primer FcF
                                      SEQ ID NO: 27
(5'-gcctccaccaagggcccatcggtcttccccctgg-3'),
and Primer PIHR
                                      SEQ ID NO: 28
(5'-cgatttgagagggagtactcac-3'),
``` thereby obtaining constant region of human IgG1.

Two PCR amplified fragments as said above were recovered and bridged, and then PCR-amplified using following primers:

NheI (5'-cctagctagccaccatgagagtgctgattctatgtggctgttcacagcctttcct-3') SEQ ID NO: 29, and Primer PIHR as mentioned above SEQ ID NO: 28.

Products were recovered from agarose gel, dual-digested by NheI and NotI (commercially available from NEB), and connected to vector pH which was dual-digested by the same enzymes to obtain expression plasmid pH-CH2B11 containing chimeric 2B11 heavy chain, which was identified through PCR and confirmed through sequencing.

6.2 Construction of Vector pK-CH2B11

PCR amplification was performed using following primers with Teasy-2B11Vκ constructed in Example 5 of the present invention as a template,

```
2BV κ F
                                      (SEQ ID NO: 30)
(5'-cttgcattcttgttgctttggtttccaggtgcaagatgtgacatcc
agatgactc-3'),
and 2BV κ R
                                      (SEQ ID NO: 31)
(5'-agccaccgtacgttttatttccaactttg-3'),
``` thereby obtaining light chain variable region of monoclonal antibody 2B11. Fragments were recovered and amplified using following primers,

```
Eco
                                      (SEQ ID NO: 32)
(5'-gatcgatatccaccatggacatgatggtccttgctcagtttcttgc
attcttgttg-3'),,
and

2BV κ R
                                      (SEQ ID NO: 31).
```

Obtained amplified products were recovered from agarose gel, dual-digested by EcoRV and BsiWI (commercially available from NEB), and connected to vector pK which was dual-digested by the same enzymes to obtain expression plasmid pK-CH2B11 containing chimeric 2B11 light chain, which was identified through PCR and confirmed through sequencing.

Example 7. Construction of Chimeric Antibody CH2B11 and Preliminary Identification of Binding Activity Thereof The expression vectors above constructed pH-CH2B11 and pK-CH2B11 were used to co-transfect CHO cells in suspension fro expression, and after 3 days, culture supernatant was collected. Expressed chimeric antibody CH2B11 was contained in the supernatant of cultured CHO cells.

Figure 7:
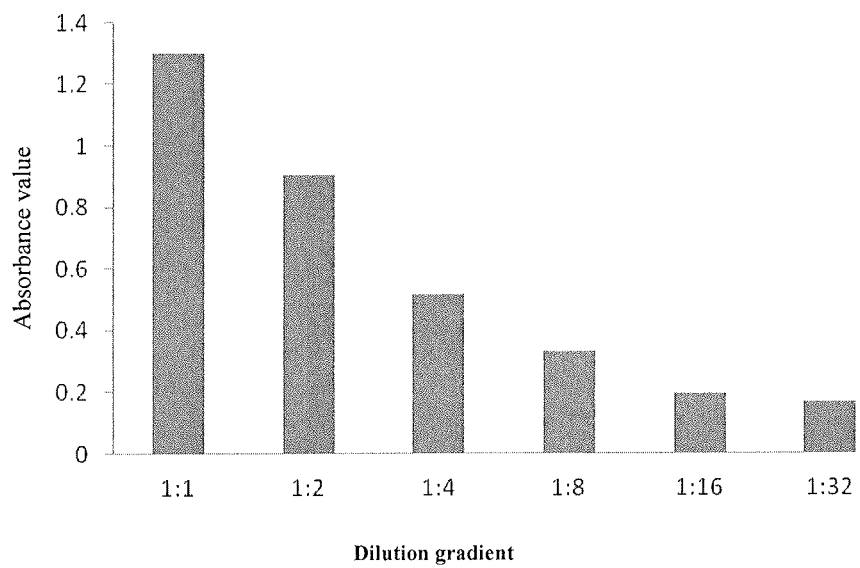
FIG. 7 shows the experimental results of binding activity of human-mouse chimeric antibody CH2B11 in Example 6 of the present invention and human proBDNF protein in Example 1 of the present invention under different diluting conditions.

The supernatant of cultured cells was taken for ELISA binding assay. The method was substantially identical with that in Example 4.4 of the present invention, except that only Experiment group 1 was included wherein human proBDNF prepared in Example 1 of the present invention was used for coating, and in each well, serial dilutions of cell supernatant of this Example were added instead of clones of corresponding 8 monoclonal antibodies. Similarly, when the absorbance value is greater than the reading in the negative control well by three times, it was identified as positive. Experiment results are shown in FIG. 7, for chimeric antibody CH2B1, the supernatant of cultured CHO cells in a dilution of 1:32 still exhibited binding activity to human proBDNF.

Example 8. Analgesic Effects of Monoclonal Antibody 2B11

8.1 Formalin-Induced Biphasic Pain can be Reduced by Intravenous Injection of 2B11

SD rats (weighing 200-250 g) were divided into 2B11 group and control group (in this experiment, the same volume of PBS was used as a control group). Modeling was mainly established by injecting 50 ul of 1% formalin into planta pedis of a mouse. At 0.5 hours before modeling, 2B11 (75 μg/kg) or placebo in an equal amount was injected via tail vein. Administration via tail vein was performed as follows: tail of a rat was washed with warm water, the site for injection was disinfected by using iodine complex, and 1 ML sterile syringe loaded with an injection dosage of antibody was used to puncture the tail vein at an angle about 10 degree parallel to the tail with slightly negative pressure. When there was a breakthrough sense and dark red blood flowed back into the syringe, 2B11 was injected in a concentration of 500 ug/kg and a total amount of 300 μL. Modeling method of formalin inflammatory pain can be mainly found in Bellasio S et al., that is, a mouse is firstly placed in a transparent Plexiglas box (30×20×20 cm) for adapting for 30 mins, and afterwards, 50 ul of 1% formalin solution is injected into planta of its right hind foot via subcutaneous injection. Upon injection, the mouse is immediately placed back into the box, the time of the mouse licking and biting the injected foot was recorded for 1 hour with 5 mins as time interval. Subcutaneous injection of formalin in plantar is a classic model of acute inflammatory pain, and in the model, there will be a special animal spontaneous pain behavior, that is, licking and biting foot. And the longer the time of licking or biting foot, the higher the intensity of pain. Such spontaneous pain behavior can generally be divided into two phases, the first phase appears at 0-5 mins after injection, the second phase appears at 15-60 mins after injection, and there will be an intermittent period between the two phases, wherein the second phase is considered as being relevant to pain sensitization (central sensitization) mechanism.

Figure 8:
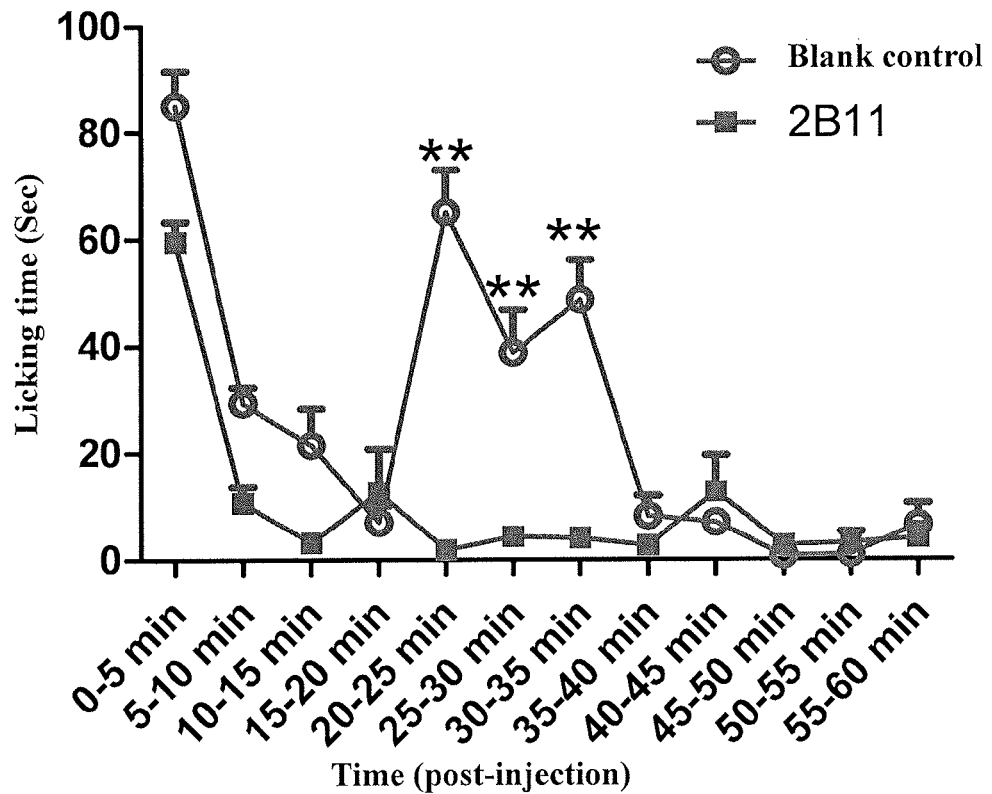
FIG. 8 shows, compared with blank control, effects of 2B11 injected via tail vein on biphasic pain induced by formalin and represented by licking time of SD rat.

According to FIG. 8 and corresponding data in the following table 1, it is shown that, in 2B11 group, the licking time of the first phase is shorter than that of the control group; while for the second phase, the licking time of the animal in 2B11 group is significantly reduced as compared with the control group, indicating that 2B11 possesses obvious analgesic effect on the formalin-caused second phase. (**, $P<0.01$, compared with the control group).

TABLE 1

| | Licking time of the control group (sec) | | | | | | Means | Licking time of 2B11 group (sec) | | | | | | Means |
|---|---|---|---|---|---|---|---|---|---|---|---|---|---|---|
| 0-5 min | 75 | 64 | 104 | 104 | 85 | 78 | 85.0 | 54 | 71 | 64 | 65 | 58 | 45 | 59.5 |
| 5-10 min | 39 | 19 | 25 | 25 | 34 | 34 | 29.3 | 9 | 22 | 0 | 6 | 15 | 12 | 10.7 |
| 10-15 min | 2 | 0 | 39 | 29 | 23 | 36 | 21.5 | 2 | 0 | 10 | 0 | 0 | 7 | 3.2 |
| 15-20 min | 0 | 0 | 9 | 7 | 5 | 21 | 7.0 | 44 | 0 | 32 | 0 | 0 | 0 | 12.7 |
| 20-25 min | 52 | 33 | 82 | 82 | 75 | 67 | 65.2 | 0 | 0 | 0 | 0 | 5 | 6 | 1.8 |
| 25-30 min | 13 | 23 | 33 | 54 | 65 | 45 | 38.8 | 0 | 2 | 10 | 1 | 8 | 5 | 4.3 |
| 30-35 min | 16 | 45 | 65 | 65 | 45 | 56 | 48.7 | 9 | 1 | 0 | 0 | 5 | 10 | 4.2 |
| 35-40 min | 16 | 0 | 0 | 0 | 21 | 12 | 8.2 | 0 | 0 | 0 | 0 | 6 | 10 | 2.7 |
| 40-45 min | 2 | 0 | 9 | 9 | 10 | 12 | 7.0 | 0 | 0 | 43 | 5 | 21 | 8 | 12.8 |
| 45-50 min | 0 | 0 | 0 | 0 | 5 | 0 | 0.8 | 0 | 1 | 0 | 0 | 6 | 10 | 2.8 |
| 50-55 min | 0 | 0 | 0 | 0 | 6 | 0 | 1.0 | 0 | 0 | 0 | 9 | 10 | 0 | 3.2 |
| 55-60 min | 27 | 0 | 2 | 2 | 5 | 3 | 6.5 | 6 | 0 | 14 | 0 | 0 | 5 | 4.2 |

8.2 Intravenous Injection of 2B11 Alleviates CFA (Complete Freund's Adjuvant)-Induced Chronic Inflammatory Pain The present experiment observes effects of 2B11 on CFA-induced chronic inflammatory pain. Pain induced by plantar injection of CFA is a classic model of chronic inflammatory pain, which is of long duration. Upon plantar injection of CFA, mechanical pain threshold of the rats is reduced for over 3 weeks.

Experiment grouping is the same as Example 8.1. The day before modeling, Von Frey filaments method was employed to observe Paw Withdrawal Threshold (PWT). Von frey filament was designed in 1896 by Maximilian von Frey, which is a tactile measuring device. Contacting wires were made of nylon filaments of different diameters, and when using these filaments, they come into contact with the skin (or other sites to be tested, such as planta of an animal) and the filaments were bent to form S-shape by applying a force. Since the strength for bending the filaments can be considered as being continuous, these filaments can accurately reflect the strength applied to the area to be measured. Currently, Von frey filament is one of the most commonly used tools for measuring all kinds of post-pain mechanical hyperalgesia.

The method for measuring pain threshold by using von frey filaments on rat or mouse's hind legs are described in detail as follows:

According to the method of Chapland et al., rats were placed on an elevated grid-like metal mesh, so that the hind planta can be freely accessible to the operator, the rats were covered with a transparent organic glass shield, and the rats adapted to the environment for 30 mins before the start of the experiment, until carding and exploration activities of the rats substantially disappeared. The experiment was performed at 8:00-16:00, when the brightness is sufficient, the environment is quiet, and the temperature is suitable.

Before the start of the experiment, the Up and Down method [dixon, Dixon W J. Efficient analysis of experimental observations. Annu Rev Pharmacol Toxicol, 1980, 20: 441-62] was employed, and 9 Von frey filaments with different intensities (0.6, 1, 1.4, 2, 4, 6, 8, 10, 15 g) was used to bottom-up and vertically stimulate central region of plantar surface of rat's injured lateral paw (started from 2G). The filaments were bent to form S-shape for 6-8 seconds with an interval of 30 seconds between two adjacent stimulus for returning the behavioral response caused by the last stimulus to normal. Flinching reflex of rat's injured lateral paw was observed, and a positive reaction was recorded if quick flinching reflex appears during the stimulation time or immediately after the removal of von Frey filaments. However, flinching reflex caused by physical activities such as movement, can not be recorded as a positive reaction, and under such situation, the measurement shall be repeated. If the rat does not exhibit such positive reaction, a filament with a larger scale will be selected to stimulate the rat's planta; if the rat exhibits such positive reaction, a filament with a smaller scale will be selected to stimulate the rat's planta, and so on, wherein upper and lower limits of the stimulus were 15 G and 0.6 G respectively. 50% PWT was calculated according to Up and down method recommended by Dixon. A positive reaction was recorded if quick flinching reflex or licking response appears during the detection or at the moment when von Frey filaments were removed, and represented as "X". If no response was observed, it is deemed as a negative reaction, and represented as "0". According to the above test method, a sequence consisting of a combination of "0" and "X" can be obtained. "0" in front of "X" was deemed as starting point, and 6 consecutive stimulating responses were selected, such as "OXOXOO", as the key sequence for estimating 50% PWT. However, the sequence composition is not only fixed to 6 times. According to the response from rats to filaments with different intensities, the minimal sequence composition can be 4 times, such as "XXXX", wherein stimulus of rats occurred in a range of 2.0-0.6 g were positive; or can be 6 times, wherein stimulus occurred in a range of 2.0-0.6 g were negative. 50% PWT of rats with continuous positive or negative response were identified as 0.6 G and 15 G; and 50% PWT of rats with positive and negative response were calculated according to the following equation:

$$50\% \text{ g threshold} = (10^{[Xf+k\delta]})/10{,}000$$

wherein Xf=Logarithm of the last filament causing positive reaction (labeled on filament); K=constant under positive response/negative response combination (see tables); δ=mean difference between stimuli (Logarithm, 0.224 herein).

TABLE 2

| Pattern | Value for k |
|---|---|
| OX | −0.5 |
| OOX | −0.388 |
| OOOX | −0.378 |
| OOOOX | −0.377 |
| OXO | 0.842 |
| OOXO | 0.89 |
| OOOXO | 0.894 |
| OOOOXO | 0.894 |
| OXX | −0.178 |

TABLE 2-continued

| Pattern | Value for k |
|---|---|
| OOXX | 0 |
| OOOXX | 0.026 |
| OOOOXX | 0.028 |
| OXOO | 0.299 |
| OOXOO | 0.314 |
| OOOXOO | 0.315 |
| OOOOXOO | 0.315 |
| OXOX | −0.5 |
| OOXOX | −0.439 |
| OOOXOX | −0.432 |
| OOOOXOX | −0.432 |
| OXXO | 1 |
| OOXXO | 1.122 |
| OOOXXO | 1.139 |
| OOOOXXO | 1.14 |
| OXXX | 0.194 |
| OOXXX | 0.449 |
| OOOXXX | 0.5 |
| OOOOXXX | 0.506 |
| OXOOO | −0.157 |
| OOXOOO | −0.154 |
| OOOXOOO | −0.154 |
| OOOOXOOO | −0.154 |
| OXOOX | −0.878 |
| OOXOOX | −0.861 |
| OOOXOOX | −0.86 |
| OOOOXOOX | −0.86 |
| OXOXO | 0.701 |
| OOXOXO | 0.737 |
| OOOXOXO | 0.741 |
| OOOOXOXO | 0.741 |
| OXOXX | 0.084 |
| OOXOXX | 0.169 |
| OOOXOXX | 0.181 |
| OOOOXOXX | 0.182 |
| OXXOO | 0.305 |
| OOXXOO | 0.372 |
| OOOXXOO | 0.38 |
| OOOOXXOO | 0.381 |
| OXXOX | −0.305 |
| OOXXOX | −0.169 |
| OOOXXOX | −0.144 |
| OOOOXXOX | −0.142 |
| OXXXO | 1.288 |
| OOXXXO | 1.5 |
| OOOXXXO | 1.544 |
| OOOOXXXO | 1.549 |
| OXXXX | 0.555 |
| OOXXXX | 0.897 |
| OOOXXXX | 0.985 |
| OOOOXXXX | 1 |
| OXOOOO | −0.547 |
| OOXOOOO | −0.547 |
| OOOXOOOO | −0.547 |
| OOOOXOOOO | −0.547 |
| OXOOOX | −1.25 |
| OOXOOOX | −1.247 |
| OOOXOOOX | −1.246 |
| OOOOXOOOX | −1.246 |
| OXOOXO | 0.372 |
| OOXOOXO | 0.38 |
| OOOXOOXO | 0.381 |
| OOOOXOOXO | 0.381 |
| OXOOXX | −0.169 |
| OOXOOXX | −0.144 |
| OOOXOOXX | −0.142 |
| OOOOXOOXX | −0.142 |
| OXOXOO | 0.022 |
| OOXOXOO | 0.039 |
| OOOXOXOO | 0.04 |
| OOOOXOXOO | 0.04 |
| OXOXOX | −0.5 |
| OOXOXOX | −0.458 |
| OOOXOXOX | −0.453 |
| OOOOXOXOX | −0.453 |
| OXOXXO | 1.169 |
| OOXOXXO | 1.237 |
| OOOXOXXO | 1.247 |

TABLE 2-continued

| Pattern | Value for k |
|---|---|
| OOOOXOXXO | 1.248 |
| OXOXXX | 0.611 |
| OOXOXXX | 0.732 |
| OOOXOXXX | 0.756 |
| OOOOXOXXX | 0.758 |
| OXXOOO | −0.296 |
| OOXXOOO | −0.266 |
| OOOXXOOO | −0.263 |
| OOOOXXOOO | −0.263 |
| OXXOOX | −0.831 |
| OOXXOOX | −0.763 |
| OOOXXOOX | −0.753 |
| OOOOXXOOX | −0.752 |
| OXXOXO | 0.831 |
| OOXXOXO | 0.935 |
| OOOXXOXO | 0.952 |
| OOOOXXOXO | 0.954 |
| OXXOXX | 0.296 |
| OOXXOXX | 0.463 |
| OOOXXOXX | 0.5 |
| OOOOXXOXX | 0.504 |
| OXXXOO | 0.5 |
| OOXXXOO | 0.648 |
| OOOXXXOO | 0.678 |
| OOOOXXXOO | 0.681 |
| OXXXOX | −0.043 |
| OOXXXOX | 0.187 |
| OOOXXXOX | 0.244 |
| OOOOXXXOX | 0.252 |
| OXXXXO | 1.603 |
| OOXXXXO | 1.917 |
| OOOXXXXO | 2 |
| OOOOXXXXO | 2.014 |
| OXXXXX | 0.893 |
| OOXXXXX | 1.329 |
| OOOXXXXX | 1.465 |
| OOOOXXXXX | 1.496 |
| XO | 0.5 |
| XXO | 0.388 |
| XXXO | 0.378 |
| XXXXO | 0.377 |
| XOX | −0.842 |
| XXOX | −0.89 |
| XXXOX | −0.894 |
| XXXXOX | −0.894 |
| XOO | 0.178 |
| XXOO | 0 |
| XXXOO | −0.026 |
| XXXXOO | −0.028 |
| XOXX | −0.299 |
| XXOXX | −0.314 |
| XXXOXX | −0.315 |
| XXXXOXX | −0.315 |
| XOXO | 0.5 |
| XXOXO | 0.439 |
| XXXOXO | 0.432 |
| XXXXOXO | 0.432 |
| XOOX | −1 |
| XXOOX | −1.122 |
| XXXOOX | −1.139 |
| XXXXOOX | −1.14 |
| XOOO | −0.194 |
| XXOOO | −0.449 |
| XXXOOO | −0.5 |
| XXXXOOO | −0.506 |
| XOXXX | 0.157 |
| XXOXXX | 0.154 |
| XXXOXXX | 0.154 |
| XXXXOXXX | 0.154 |
| XOXXO | 0.878 |
| XXOXXO | 0.861 |
| XXXOXXO | 0.86 |
| XXXXOXXO | 0.86 |
| XOXOX | −0.701 |
| XXOXOX | −0.737 |
| XXXOXOX | −0.741 |
| XXXXOXOX | −0.741 |
| XOXOO | −0.084 |

TABLE 2-continued

| Pattern | Value for k |
|---|---|
| XXOXOO | −0.169 |
| XXXOXOO | −0.181 |
| XXXXOXOO | −0.182 |
| XOOXX | −0.305 |
| XXOOXX | −0.372 |
| XXXOOXX | −0.38 |
| XXXXOOXX | −0.381 |
| XOOXO | 0.305 |
| XXOOXO | 0.169 |
| XXXOOXO | 0.144 |
| XXXXOOXO | 0.142 |
| XOOOX | −1.288 |
| XXOOOX | −1.5 |
| XXXOOOX | −1.544 |
| XXXXOOOX | −1.549 |
| XOOOO | −0.555 |
| XXOOOO | −0.897 |
| XXXOOOO | −0.985 |
| XXXXOOOO | −1 |
| XOXXXX | 0.547 |
| XXOXXXX | 0.547 |
| XXXOXXXX | 0.547 |
| XXXXOXXXX | 0.547 |
| XOXXXO | 1.25 |
| XXOXXXO | 1.247 |
| XXXOXXXO | 1.246 |
| XXXXOXXXO | 1.246 |
| XOXXOX | −0.372 |
| XXOXXOX | −0.38 |
| XXXOXXOX | −0.381 |
| XXXXOXXOX | −0.381 |
| XOXXOO | 0.169 |
| XXOXXOO | 0.144 |
| XXXOXXOO | 0.142 |
| XXXXOXXOO | 0.142 |
| XOXOXX | −0.022 |
| XXOXOXX | −0.039 |
| XXXOXOXX | −0.04 |
| XXXXOXOXX | −0.04 |
| XOXOXO | 0.5 |
| XXOXOXO | 0.458 |
| XXXOXOXO | 0.453 |
| XXXXOXOXO | 0.453 |
| XOXOOX | −1.169 |
| XXOXOOX | −1.237 |
| XXXOXOOX | −1.247 |
| XXXXOXOOX | −1.248 |
| XOXOOO | −0.611 |
| XXOXOOO | −0.732 |
| XXXOXOOO | −0.756 |
| XXXXOXOOO | −0.758 |
| XOOXXX | 0.296 |
| XXOOXXX | 0.266 |
| XXXOOXXX | 0.263 |
| XXXXOOXXX | 0.263 |
| XOOXXO | 0.831 |
| XXOOXXO | 0.763 |
| XXXOOXXO | 0.753 |
| XXXXOOXXO | 0.752 |
| XOOXOX | −0.831 |
| XXOOXOX | −0.935 |
| XXXOOXOX | −0.952 |
| XXXXOOXOX | −0.954 |
| XOOXOO | −0.296 |
| XXOOXOO | −0.463 |
| XXXOOXOO | −0.5 |
| XXXXOOXOO | −0.504 |
| XOOOXX | −0.5 |
| XXOOOXX | −0.648 |
| XXXOOOXX | −0.678 |
| XXXXOOOXX | −0.681 |
| XOOOXO | 0.043 |
| XXOOOXO | −0.187 |
| XXXOOOXO | −0.244 |
| XXXXOOOXO | −0.252 |
| XOOOOX | −1.603 |
| XXOOOOX | −1.917 |
| XXXOOOOX | −2 |
| XXXXOOOOX | −2.014 |
| XOOOOO | −0.983 |
| XXOOOOO | −1.329 |
| XXXOOOOO | −1.465 |
| XXXXOOOOO | −1.496 |

Values for k, based on response pattern (modified from Dixon, 1980)

In each experiment group, 100 μL of CFA was injected to mice at planta, and then 2B11 (75 kg/kg/day) or PBS were given via tail vein, one time every 12 hours until the $5^{th}$ day after the injection of CFA. Upon injection, changes in PWT were observed at different time periods to the fifth day after operation.

Figure 9:
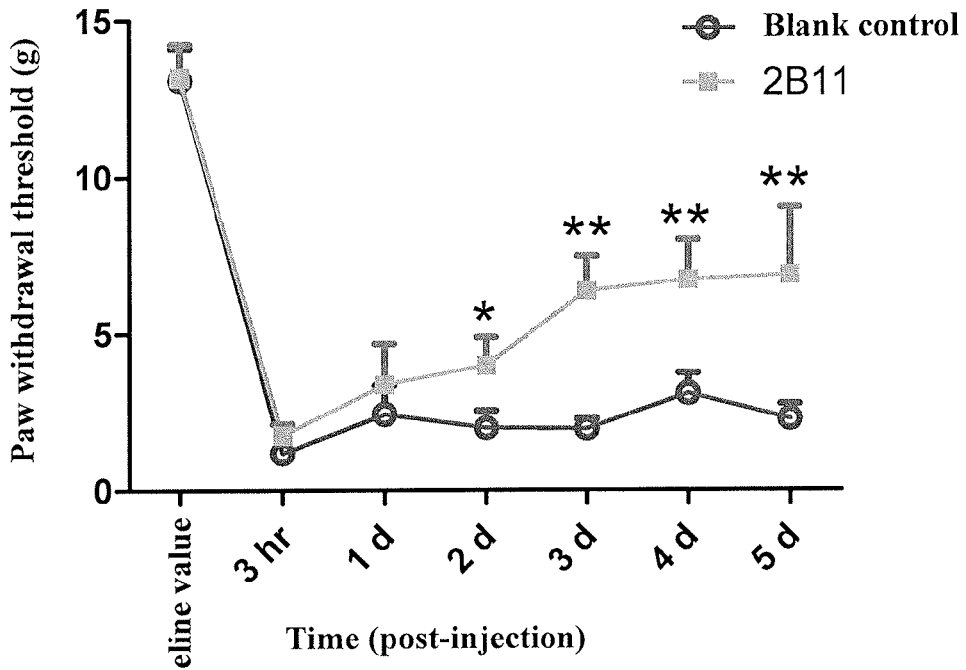
FIG. 9 shows, compared with blank control, effects of 2B11 injected via tail vein on chronic persistent inflammatory pain induced by plantar injection of CFA.

According to FIG. 9 and corresponding data in the following table 3, it is shown that, in the blank control group, after injection of CFA at planta, withdrawal threshold PWT of hind paw was significantly reduced, compared with baseline value, until the $5^{th}$ day after the injection; while in the 2B11 group, at the $2^{nd}$ day after injection of CFA, the pain threshold of mice was significantly improved, compared with the blank control group, PWT values gradually increased, and at the $5^{th}$ day after injection, in 2B11 group, PWT was significantly higher than that in the blank control group, which demonstrates that 2B11 can significantly reduce chronic inflammatory pain caused by CFA (FIG. 9). *, $P<0.05$, compared with control group; **, $P<0.01$ compared with the control group.

TABLE 3

| | Paw withdrawal threshold, control group (g) | | | | | | | Means | Paw withdrawal threshold, 2B11 group (g) | | | | | | | Means |
|---|---|---|---|---|---|---|---|---|---|---|---|---|---|---|---|---|
| Baseline value | 15 | 15 | 15 | 15 | 12.99 | 8.61 | 10.04 | 13.1 | 15 | 15 | 15 | 11.88 | 15 | 7.53 | 12.99 | 13.2 |
| 3 hr | 1.72 | 1.58 | 0.6 | 1.08 | 1.46 | 0.92 | 0.99 | 1.2 | 3.33 | 1.58 | 2.27 | 1.72 | 0.6 | 2.27 | 0.6 | 1.8 |
| 1 d | 1.22 | 2.27 | 2.7 | 0.86 | 0.92 | 1.22 | 7.8 | 2.4 | 2.27 | 0.6 | 1.91 | 1.46 | 1.22 | 10.04 | 6.17 | 3.4 |
| 2 d | 1.08 | 5.04 | 1.22 | 1.91 | 0.6 | 1.61 | 2.47 | 2.0 | 3.73 | 2.03 | 4.4 | 0.82 | 4.25 | 8.44 | 4.25 | 4.0 |
| 3 d | 2.27 | 2.27 | 2.81 | 0.86 | 0.86 | 2.81 | 1.91 | 2.0 | 5.04 | 5.04 | 6.64 | 2.03 | 6.64 | 11.69 | 7.53 | 6.4 |
| 4 d | 6.66 | 2.81 | 2.37 | 3.33 | 1.91 | 1.45 | 3.13 | 3.1 | 7.8 | 3.58 | 8.44 | 2 | 10.04 | 10.69 | 4.47 | 6.7 |
| 5 d | 2.81 | 2.27 | 3.73 | 1.58 | 1.01 | | | 2.3 | 6.58 | 15 | | 5.57 | 4.98 | 2.27 | | 6.9 |

8.3 Effects of Intravenous Injection of 2B11 on Cutting Pain

Cutting pain model of rat hind paws is the most commonly used animal model for surgical pain. After cutting at hind paws, rats elevate the cut limb, can not bear weight, while lick the paw. Therefore, pain score is often used to elevate the degree of cutting pain. Rats were observed for grounding situation, every 5 minutes (generally calculated in hours). If the hind paw was always elevated, it will be given 2 points; if the rat can ground, but can not bear weight (whether the mesh of the cage is deformed is used as a criterion), it will be given 1 point; and if the rat can completely ground and bear weight, it will be given 0 point. The higher the score, the stronger the degree of pain. Cumulative Pain Score (CPS) is often employed to evaluate the degree of cutting pain of foot. The higher the CPS, the stronger the intensity of pain. On the other hand, after cutting, mechanical pain threshold will fall accordingly. Therefore, we use these two methods to evaluate effects of proBDNF monoclonal antibody (2B11) on cutting pain.

Figure 10:
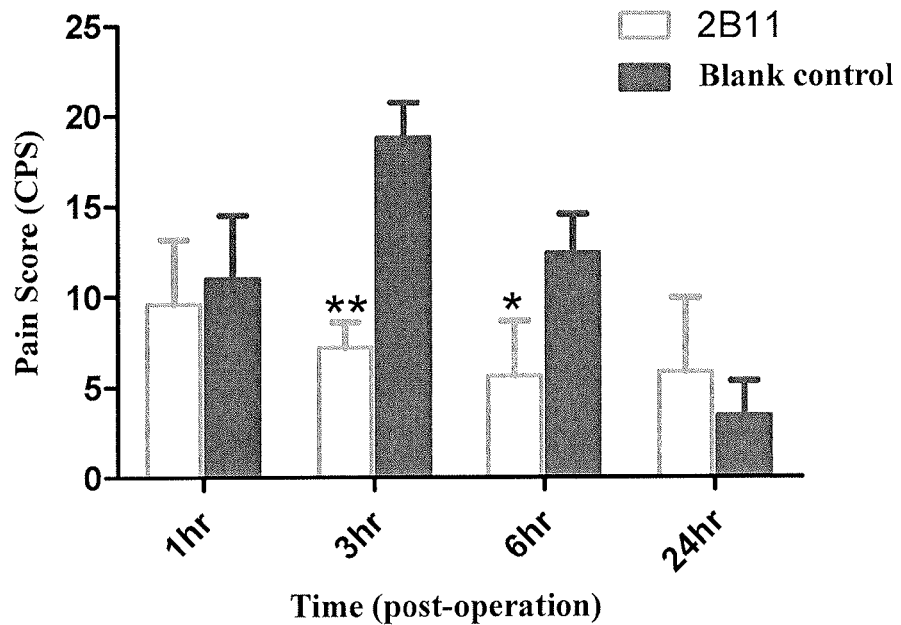
FIG. 10 shows, compared with blank control, effects of 2B11 injected via tail vein on pain score of cutting pain of a rat's hinder legs.
Figure 11:
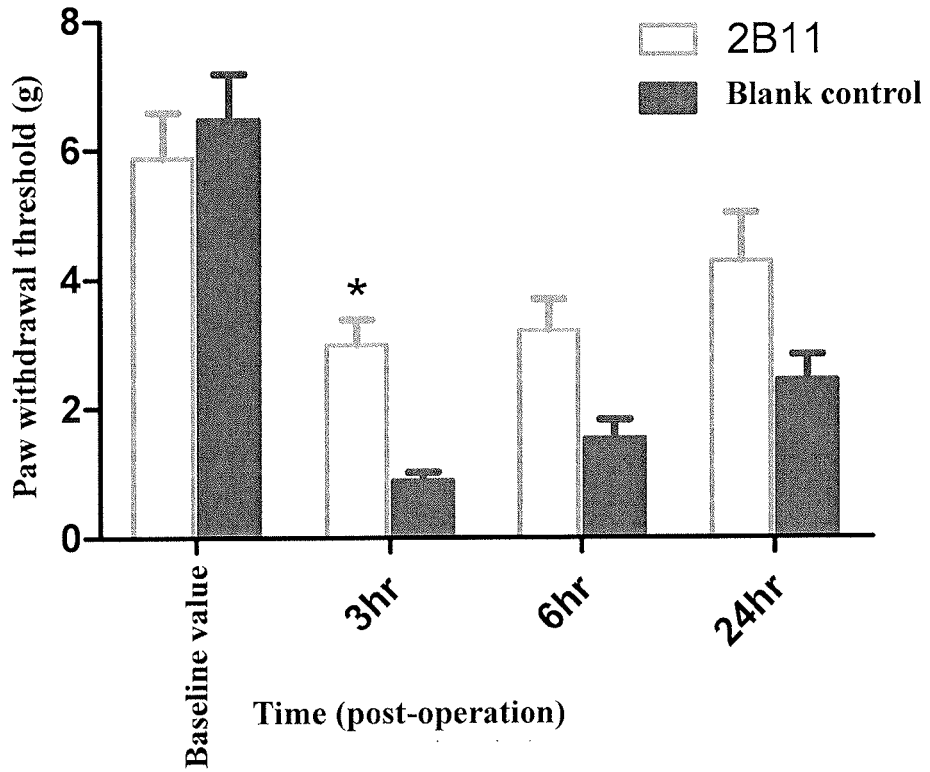
FIG. 11 shows, compared with blank control, effects of 2B11 injected via tail vein on area of mechanical pain of cutting pain of a rat's hinder legs.

Experiment grouping is the same as Example 8.1. At 15 minutes before the operation, 500 ug/kg of 2B11 was given via intravenous injection. Rats were observed for pain score (FIG. 10 and following table 4) and mechanical pain threshold of hind paw (FIG. 11 and following table 5) at different time periods after operation, and it can be found that:

In 2B11 experiment group, pain scores of mouse measured at 1 hour after the cutting operation were significantly lower compared with the mouse in the control group, wherein the difference at 3 hour after the cutting operation was the most significant. And pain scores measured at 6 hour after the cutting operation were still significantly lower than those of the control group.

TABLE 4

| | Pain scores of 2B11 group (cps) | | | | | Means | Pain scores of control group (cps) | | | | | Means |
|---|---|---|---|---|---|---|---|---|---|---|---|---|
| 1 hr | 1 | 20 | 9 | 15 | 3 | 9.6 | 5 | 9 | 24 | 12 | 5 | 11 |
| 3 hr | 4 | 11 | 9 | 8 | 4 | 7.2 | 21 | 13 | 24 | 20 | 16 | 18.8 |
| 6 hr | 1 | 17 | 7 | 1 | 2 | 5.6 | 8 | 13 | 18 | 16 | 7 | 12.4 |
| 24 hr | 2 | 22 | 2 | 0 | 3 | 5.8 | 0 | 0 | 9 | 7 | 1 | 3.4 |

In 2B11 experiment group, mechanical pain threshold of mouse measured at 1 hour after the cutting operation were significantly lower compared with the mouse in the control group.

TABLE 5

| | Paw withdrawal threshold, 2B11 group (g) | | | | | Means | Paw withdrawal threshold, control group (g) | | | | | Means |
|---|---|---|---|---|---|---|---|---|---|---|---|---|
| Baseline value | 7.8 | 4.25 | 4.25 | 4.74 | 8 | 6.23 | 5.88 | 8.61 | 4.25 | 7.8 | 6.81 | 4.56 | 6.81 | 6.47 |
| 3 hr | 4.25 | 2.75 | 2.1 | 2.03 | 4.14 | 2.65 | 2.99 | 0.89 | 0.6 | 0.6 | 0.6 | 1.45 | 1.1 | 0.87 |
| 6 hr | 2.81 | 1.22 | 3.73 | 3.58 | 4.72 | 3.21 | 3.21 | 0.86 | 1.45 | 0.6 | 2.03 | 2.27 | 2.03 | 1.54 |
| 24 hr | 2.03 | 4.7 | 1.99 | 5.56 | 6.17 | 5.23 | 4.28 | 2.27 | 1.36 | 2 | 2.37 | 4.25 | 2.37 | 2.44 |

From the results of the above Table 4 and 5, it is demonstrated that the monoclonal antibody 2B11 of the invention has a good and significant analgesic effect on cutting pain.

8.4 Visceral Pain Induced by Intraperitoneal Injection of Acetic Acid was Reduced by Intraperitoneal Injection of 2B11.

Upon intraperitoneal injection of acetic acid, mice mainly exhibit writhing responses, such as abdominal contraction, stretching (Writhing Test), especially at 1 hour after injection. Observation of writhing responses during 1 hour after the injection of acetic acid is a commonly used model for screening analgesics. Intraperitoneal injection of 0.6% acetic acid (0.2 ml) per mouse will cause chemical visceral pain.

Experiment grouping is the same as Example 8.1. At 30 minutes before the injection of acetic acid, monoclonal antibody 2B11 (500 ug/kg, 0.2 ml) or placebo in the same volume (herein referring to PBS) was given to mice in each experiment groups via intraperitoneal injection respectively.

Figure 12:
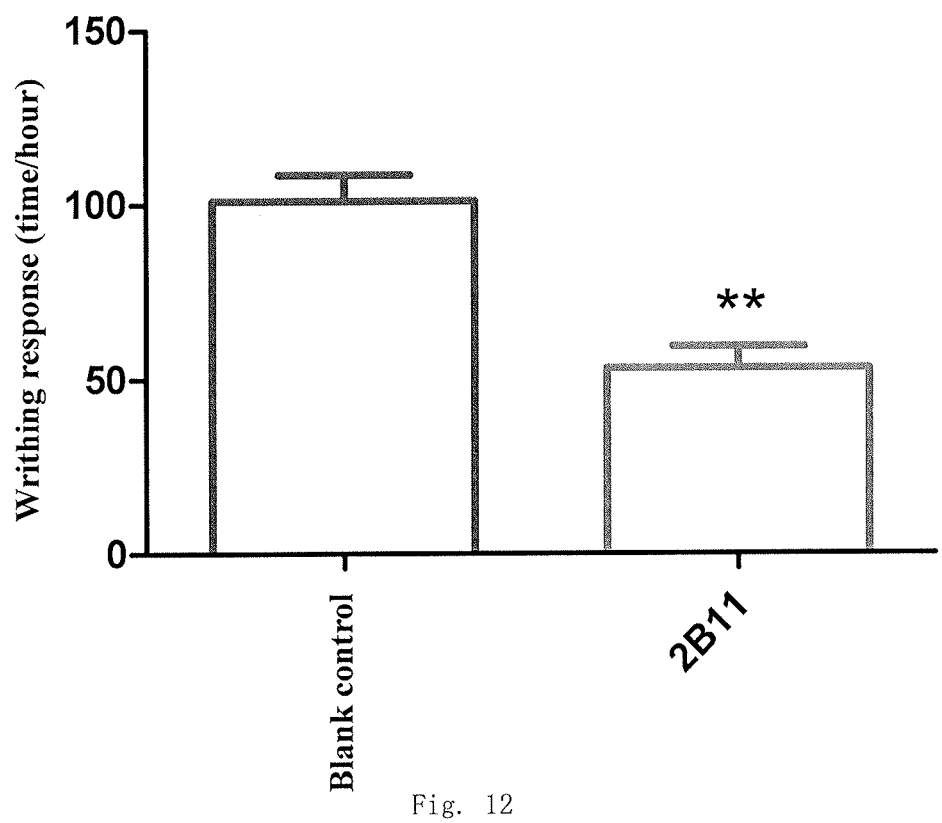
FIG. 12 shows, compared with blank control, effects of 2B11 intraperitoneally injected on writhing response induced by acetic acid in a mouse.

According to FIG. 12 and corresponding data in the following table 6, it is shown that, compared with the mice in the control group, writhing responses of the mice in 2B11 group are significantly reduced, which demonstrates that pre-treatment of monoclonal antibody 2B11 of the present invention can reduce visceral pain induced by intraperitoneal injection of acetic acid.

TABLE 6

|  | Writhing response in control group (time/hour) | Writhing response in 2B11 group (times/hour) |
| --- | --- | --- |
|  | 117 | 74 |
|  | 78 | 58 |
|  | 90 | 57 |
|  | 95 | 47 |
|  | 137 | 62 |
|  | 89 | 53 |
|  | 101 | 22 |
| Means | 101 | 53.3 |

The invention claimed is:

1. An antibody polypeptide that specifically recognizes the pro-BDNF pro-domain, including
   1) a heavy chain variable region comprising the following amino acid sequences:
      (a) CDR1 region of SEQ ID NO: 1,
      (b) CDR2 region of SEQ ID NO: 2, and
      (c) CDR3 region of SEQ ID NO: 3; and
   2) a light chain variable region comprising the following amino acid sequences:
      (d) CDR1 region of SEQ ID NO: 4,
      (e) CDR2 region of SEQ ID NO: 5, and
      (f) CDR3 region of SEQ ID NO: 6.

2. The antibody polypeptide of claim 1, wherein the antibody polypeptide is a monoclonal antibody.

3. The antibody polypeptide of claim 2, wherein the antibody polypeptide is selected from a humanized antibody polypeptide, a chimeric antibody polypeptide, an affinity maturated antibody polypeptide or one or more combinations thereof.

4. The antibody polypeptide of claim 1, wherein the amino acid sequence of the heavy chain variable region is SEQ ID NO: 7.

5. The antibody polypeptide of claim 4, wherein the amino acid sequence of the light chain variable region is SEQ ID NO: 8.

6. The antibody polypeptide of claim 1, wherein the amino acid sequence of the heavy chain is SEQ ID NO: 9.

7. The antibody polypeptide of claim 6, wherein the amino acid sequence of the light chain is SEQ ID NO: 10.

8. A method for mitigating and/or inhibiting pain selected from the group consisting of post-operative pain, acute inflammatory pain, chronic inflammatory pain, phantom limb pain, painful diabetic neuropathy, neuropathic pain, chronic lumbodorsalgia, chronic visceral pain, cancer pain, arthritis pain, craniofacial pain, trigeminal neuralgia, migraine, complex regional pain syndrome, and a combination thereof, the method comprising administering the antibody polypeptide of claim 1.

9. A pharmaceutical composition comprising a therapeutically effective amount of the antibody polypeptide of claim 1.

10. The pharmaceutical composition of claim 9, which is administered by intravenous or intraperitoneal injection.

11. A monoclonal antibody polypeptide that specifically recognizes the pro-BDNF pro-domain, including
   1) a heavy chain variable region comprising the following amino acid sequences:
      (a) CDR1 region of SEQ ID NO: 1,
      (b) CDR2 region of SEQ ID NO: 2, and
      (c) CDR3 region of SEQ ID NO: 3; and
   2) a light chain variable region comprising the following amino acid sequences:
      (d) CDR1 region of SEQ ID NO: 4,
      (e) CDR2 region of SEQ ID NO: 5, and
      (f) CDR3 region of SEQ ID NO: 6;
      wherein the antibody polypeptide comprises a conservative amino acid substitution within the CDR1, CDR2, or CDR3 region of the heavy chain variable region or the light chain variable region.

12. A nucleic acid encoding an antibody polypeptide that specifically recognizes the pro-BDNF pro-domain, including:
   1) a heavy chain variable region comprising the following amino acid sequences:
      (a) CDR1 region of SEQ ID NO: 1,
      (b) CDR2 region of SEQ ID NO: 2, and
      (c) CDR3 region of SEQ ID NO: 3; and
   2) a light chain variable region comprising the following amino acid sequences:
      (d) CDR1 region of SEQ ID NO: 4,
      (e) CDR2 region of SEQ ID NO: 5, and
      (f) CDR3 region of SEQ ID NO: 6.

13. The nucleic acid of claim 12, comprising a nucleic acid having the sequence set forth in SEQ ID NO: 11 encoding the amino acid sequence of the heavy chain variable region of the antibody polypeptide and a nucleic acid having the sequence set forth in SEQ ID NO: 12 encoding the amino acid sequence of the light chain variable region of the antibody polypeptide.

14. The nucleic acid of claim 13, comprising a nucleic acid having the sequence set forth in SEQ ID NO:13 encoding the amino acid sequence of the heavy chain of the antibody polypeptide and a nucleic acid having the sequence set forth in SEQ ID NO:14 encoding the amino acid sequence of the light chain of the antibody polypeptide.

15. A vector comprising a nucleic acid encoding an antibody polypeptide that specifically recognizes the pro-BDNF pro-domain, including:
   1) a heavy chain variable region comprising the following amino acid sequences:
      (a) CDR1 region of SEQ ID NO: 1,
      (b) CDR2 region of SEQ ID NO: 2, and
      (c) CDR3 region of SEQ ID NO: 3; and
   2) a light chain variable region comprising the following amino acid sequences:
      (d) CDR1 region of SEQ ID NO: 4,
      (e) CDR2 region of SEQ ID NO: 5, and
      (f) CDR3 region of SEQ ID NO: 6.

16. A host comprising a vector comprising a nucleic acid encoding an antibody polypeptide that specifically recognizes the pro-BDNF pro-domain, including:

1) a heavy chain variable region comprising the following amino acid sequences:
   (a) CDR1 region of SEQ ID NO: 1,
   (b) CDR2 region of SEQ ID NO: 2, and
   (c) CDR3 region of SEQ ID NO: 3; and
2) a light chain variable region comprising the following amino acid sequences:
   (d) CDR1 region of SEQ ID NO: 4,
   (e) CDR2 region of SEQ ID NO: 5, and
   (f) CDR3 region of SEQ ID NO: 6.

\* \* \* \* \*